United States Patent
Ueda et al.

(10) Patent No.: US 9,796,853 B2
(45) Date of Patent: *Oct. 24, 2017

(54) WATER-ABSORBENT RESIN COMPOSITION AND METHOD FOR PRODUCING THEREOF, AND ABSORBENT MATERIAL AND ABSORBENT PRODUCT USING THEREOF

(75) Inventors: Hiroko Ueda, Himeji (JP); Katsuyuki Wada, Himeji (JP); Yasuhisa Nakashima, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 1559 days.

This patent is subject to a terminal disclaimer.

(21) Appl. No.: 10/565,324

(22) PCT Filed: Jul. 23, 2004

(86) PCT No.: PCT/JP2004/010896
§ 371 (c)(1),
(2), (4) Date: Jan. 20, 2006

(87) PCT Pub. No.: WO2005/010102
PCT Pub. Date: Feb. 3, 2005

(65) Prior Publication Data
US 2006/0189738 A1   Aug. 24, 2006

(30) Foreign Application Priority Data
Jul. 25, 2003 (JP) .................................. 2003-280373

(51) Int. Cl.
*C08L 101/14* (2006.01)
*A61L 15/18* (2006.01)
*A61L 15/60* (2006.01)

(52) U.S. Cl.
CPC ............. *C08L 101/14* (2013.01); *A61L 15/18* (2013.01); *A61L 15/60* (2013.01)

(58) Field of Classification Search
CPC ......... C08L 101/14; A61L 15/18; A61L 15/60
USPC ........ 524/413, 460; 428/500, 522, 257, 259, 428/270, 283, 288, 326, 360, 361, 393, 428/392, 400, 402, 903, 913; 604/358, 604/359, 367, 372, 365, 368, 374, 377; 424/76.1, 76.5, 76.6, 213; 442/398, 346; 525/329.7, 330.1, 384; 526/295, 310, 317
See application file for complete search history.

(56) References Cited

U.S. PATENT DOCUMENTS

| | | | |
|---|---|---|---|
| 2,891,865 A * | 6/1959 | Seltzer ...................... A23F 3/16 | |
| | | | 426/435 |
| 4,093,776 A | 6/1978 | Aoki et al. .................... 428/402 |
| 4,286,082 A | 8/1981 | Tsubakimoto et al. ....... 526/240 |
| 4,367,323 A | 1/1983 | Kitamura et al. ............. 526/201 |
| 4,446,261 A | 5/1984 | Yamasaki et al. .............. 524/40 |
| 4,625,001 A | 11/1986 | Tsubakimoto et al. ......... 526/88 |
| 4,683,274 A | 7/1987 | Nakamura et al. ............ 526/216 |
| 4,873,299 A | 10/1989 | Nowakowsky et al. ........ 526/73 |
| 4,954,562 A * | 9/1990 | Anderson ...................... 524/779 |
| 4,973,632 A | 11/1990 | Nagasuna et al. ............ 526/200 |
| 4,985,518 A | 1/1991 | Alexander et al. ........... 526/240 |
| 5,110,586 A * | 5/1992 | Kurihara et al. ............. 424/76.1 |
| 5,124,416 A | 6/1992 | Haruna et al. .................. 526/62 |
| 5,145,906 A | 9/1992 | Chambers et al. ............ 524/732 |
| 5,244,735 A | 9/1993 | Kimura et al. ................ 428/402 |
| 5,250,640 A | 10/1993 | Irie et al. ......................... 526/88 |
| 5,264,495 A | 11/1993 | Irie et al. ....................... 125/301 |
| 5,380,808 A | 1/1995 | Sumiya et al. ............. 526/317.1 |
| 5,684,106 A * | 11/1997 | Johnson et al. ............... 526/295 |
| 6,071,976 A | 6/2000 | Dairoku et al. ................ 521/50 |
| 6,228,930 B1 | 5/2001 | Dairoku et al. ............... 524/500 |
| 6,254,990 B1 * | 7/2001 | Ishizaki et al. ............... 428/402 |
| 6,284,362 B1 * | 9/2001 | Takai et al. ................... 428/326 |
| 6,951,895 B1 * | 10/2005 | Qin et al. ........................ 524/17 |
| 7,473,470 B2 * | 1/2009 | Ishizaki et al. ............... 428/407 |
| 7,825,169 B2 * | 11/2010 | Wada ................... A61F 13/8405 |
| | | | 523/102 |
| 2002/0120242 A1 * | 8/2002 | Tyrrell et al. ................. 604/364 |

(Continued)

FOREIGN PATENT DOCUMENTS

| | | | |
|---|---|---|---|
| EP | 0 282 287 A2 | 9/1988 | ............... A61L 9/01 |
| EP | 0 811 636 A1 | 12/1997 | ................ C08F 2/10 |
| EP | 0 922 717 A1 | 6/1999 | ........... C08F 220/04 |
| EP | 0 955 086 A2 | 11/1999 | ............. B01J 19/22 |
| EP | 1 099 474 A1 | 5/2001 | ............. B01J 20/26 |
| JP | 60-158861 | 8/1985 | ............. A61F 13/18 |
| JP | 63-135501 | 6/1988 | ............. A41B 13/02 |
| JP | 64-5546 | 1/1989 | ............. A61F 13/18 |
| JP | 02-041155 | 2/1990 | ............. A61F 13/46 |
| JP | 08-176338 | 7/1996 | ................ C08K 3/22 |
| JP | 10-147724 | 6/1998 | ........... C08L 101/14 |
| JP | 10-298442 | 11/1998 | ........... C08L 101/14 |
| JP | 11-049971 | 2/1999 | ........... C08L 101/14 |
| JP | 11-116829 | 4/1999 | ........... C08L 101/08 |
| JP | 11-148023 | 6/1999 | ........... C08L 101/08 |
| JP | 11-241030 | 9/1999 | ........... C08L 101/14 |
| WO | WO 00/01479 | 1/2000 | ............. B01J 20/26 |

*Primary Examiner* — Ling Choi
*Assistant Examiner* — David L Miller
(74) *Attorney, Agent, or Firm* — Cesari and McKenna, LLP

(57) ABSTRACT

A water-absorbent resin composition suffering exfoliation of additives from a water-absorbent resin only insignificantly and excelling in fluidity of powder after absorption of moisture and in deodorizing property and absorbent property as well is provided. The water-absorbent resin composition of this invention comprises a water-absorbent resin obtainable by polymerizing an unsaturated monomer having an acid group and/or a salt thereof; and complex oxide hydrate containing zinc and silicon, or zinc and aluminum, wherein the complex oxide hydrate contains zinc as main metal component, the mass ratio of the content of zinc and the content of silicon or aluminum is in the range of 50/50-99/1, and the absorption capacity at 60 minutes toward 0.90 mass % sodium chloride aqueous solution under the pressure of 1.9 kPa is not less than 20 g/g. Optionally, a plant component (C) can be added to the water absorbent resin composition.

20 Claims, No Drawings

(56) References Cited

U.S. PATENT DOCUMENTS

| | | | |
|---|---|---|---|
| 2003/0004479 A1* | 1/2003 | Ueda | A61L 15/40 604/359 |
| 2003/0018114 A1* | 1/2003 | Tai et al. | 524/413 |
| 2004/0048955 A1* | 3/2004 | Wada | A61F 13/8405 524/9 |
| 2005/0027268 A1* | 2/2005 | Qin et al. | 604/367 |
| 2006/0276598 A1* | 12/2006 | Wada et al. | 525/330.3 |
| 2007/0066167 A1* | 3/2007 | Wada et al. | 442/101 |
| 2008/0075937 A1* | 3/2008 | Wada et al. | 428/212 |

* cited by examiner

WATER-ABSORBENT RESIN COMPOSITION AND METHOD FOR PRODUCING THEREOF, AND ABSORBENT MATERIAL AND ABSORBENT PRODUCT USING THEREOF

CROSS-REFERENCE TO RELATED APPLICATIONS

This application is the National Stage of International Application No. PCT/JP2004/010896, filed Jul. 23, 2004, which claims the benefit of Japanese Patent Application Serial No. 2003-280373, filed on Jul. 25, 2003. The contents of both of the foregoing applications are hereby incorporated by reference in their entity.

BACKGROUND OF THE INVENTION

Field of the Invention

This invention relates to a water-absorbent resin composition, an absorbent material, and an absorbent product, and a method for the production of the water-absorbent resin composition. More particularly, this invention relates to a water-absorbent resin composition, an absorbent material, and an absorbent product which exhibit excellent hygroscopic and fluid property, separation-resistant property, deodorizing property, gel strength and absorbent property, when used as sanitary materials such as disposable diapers, sanitary napkins, and incontinence pads. This invention further relates to a method for the production of a water-absorbent resin composition possessing such characteristics.

Description of the Related Art

The water-absorbent resin is extensively used in such sanitary materials as disposable diapers, sanitary napkins, and incontinence pads with the object of absorbing such humors as urine and blood and form main components of such sanitary materials as these.

In recent years, in consequence of growth in the demand for adult disposable diapers owing particularly to the aging of the society, the desirability of imparting a deodorizing property, particularly a deodorizing property capable of eliminating offensive odors originating in such sulfur type compounds as hydrogen sulfide and mercaptans, to the water-absorbent resin has been finding growing recognition.

As a means to impart the deodorizing property to the water-absorbent resin, the combinations of the water-absorbent resin with various kinds of deodorants and antibacterial agents have been proposed. For example, a water-absorbent resin composition comprising a water-absorbent resin and the extract of leaves of the trees of theaceous plant (refer to JP-A-S60-158861, for example), an adsorbent resin composition containing the extract of coniferous trees and a water-absorbent resin possessing a specific performance (refer to JP-A-H11-241030, for example), a deodorizing resin composition having zeolite particles dispersed in a water-absorbent resin (refer to U.S. Pat. No. 5,980,879, for example), a water-absorbent resin composition formed of a water-absorbent resin and a metal-containing hydroxide comprising one element selected among titanium and zirconium and at least one element selected among zinc, aluminum, calcium, magnesium, and silicon (refer to JP-A-H10-147724, for example), a water-absorbent resin composition formed of a water-absorbent resin, an oxalate compound, and a complex silicate compound (refer to JP-A-H10-298442), a water-absorbent resin composition formed of a water-absorbent resin, a tannate, and a complex silicate compound (refer to JP-A-H11-116829, for example), a water-absorbent resin composition formed of a water-absorbent resin, a glycine type amphoteric surfactant, and a complex silicate compound (refer to JP-A-H11-49971, for example), and a water-absorbent resin composition formed of a water-absorbent resin, a sulfur-containing reducing agent, and a complex silicate compound (refer to JP-A-H11-148023, for example) have been known.

Methods for imparting a deodorizing property to absorbent products using a water-absorbent resin also have been studied. For example, an absorbent product formed of refined tea and a water-absorbent resin (refer to JP-A-H2-41155, for example), a disposable diaper containing a water-absorbent resin and a resin formed of benzalkonium chloride and/or chlorohexidine gluconate (refer to JP-A-S63-135501, for example), and a sanitary store combining a water-absorbent resin and zinc aluminosilicate (refer to JP-A-S64-5546, for example) have been known. The feasibility of imparting a deodorizing property and a powder handling property both to a water-absorbent resin also has been studied. For example, an absorbent agent formed of a water-absorbent resin, a compound possessing an antibacterial function against an ammonia-producing microbe, and a pharmaceutical preparation manifesting a neutralizing ability or a neutralizing ability and an adsorbing ability to ammonia (refer to International Publication WO00/01479) has been known. As concerns the water-absorbent resin, the improvement in the hygroscopic and fluid property (the improvement in the anti-caking property) forms an important task besides the impartation of a deodorizing property and an anti-bacterial property to the water-absorbent resin. To be specific, the water-absorbent resin has the problem of losing fluidity as powder and entailing the phenomenon of blocking during the course of absorbing humidity. The pamphlet of International Publication WO00/01479 also discloses a technique of using various additives for the purpose of solving this problem.

The deodorizing property produced by any of the aforementioned hitherto reported methods is not so great as to reach the level of manifesting a fully satisfactory deodorization in actual use. When the water-absorbent resin sacrifices the absorbent property thereof for the sake of enabling the deodorizing property thereof to be manifested to a high degree, it does not achieve the inherent object of absorbing such humors as urine and blood.

It is, therefore, an important rule to have the absorbent property exalted to a fully satisfactory level while having the deodorizing property manifested to a high degree as well.

When the water-absorbent resin incorporates additives therein for the purpose of enhancing the deodorant property and the hygroscopic and fluid property, it possibly entails such adverse phenomena as separation and exfoliation where the additives are in the form of powder. When the separation or exfoliation of such additives occurs, the additives entail formation of dust and fail to manifest the function thereof fully satisfactorily.

SUMMARY OF THE INVENTION

An object of this invention is to provide a water-absorbent resin composition, an absorbent material, and an absorbent product which entail exfoliation of additives from water-absorbent resin only insignificantly, excel in the fluidity of a powder resulting from humidification of a water-absorbent resin or a water-absorbent resin composition, possess a deodorizing property capable of satisfactorily eliminating the offensive odor originating in such sulfur type compounds as hydrogen sulfide and mercaptans, and further excel in the absorptive property. The object of this invention consists in providing a water-absorbent resin composition, an absorbent material, and an absorbent product which have a low ratio of separation of additives, excel in the hygroscopic and fluid property and in the deodorizing property, and also excel in the absorbent property. Another object of this invention is to produce a method for the production of a water-absorbent resin composition which possesses such characteristics as mentioned above.

The present inventor has pursued a diligent study with a view to solving the task mentioned above. He has consequently taken notice of the fact that the combination of a water-absorbent resin and zinc is effective in manifesting a deodorizing property. He has made a diligent study in search of conditions for enhancing the deodorizing property and enabling the excellent absorbent property and the excellent hygroscopic and fluid property to be manifested fully. He has finally found that the task can be solved by combining a water-absorbent resin possessing a prescribed absorbent property and a complex oxide hydrate containing zinc and silicon or zinc and aluminum at a prescribed ratio.

Specifically, this invention concerns a water-absorbent resin composition having the absorption capacity at 60 minutes toward 0.90 mass % sodium chloride aqueous solution under the pressure of 1.9 kPa not less than 20 g/g, comprising: absorbent resin obtainable by polymerizing an unsaturated monomer having an acid group and/or a salt thereof; and complex oxide hydrate containing zinc and silicon, or zinc and aluminum, wherein the complex oxide hydrate contains zinc as main metal component, and the mass ratio of the content of zinc and the content of silicon or aluminum is in the range of 50/50-99/1.

This Invention Also Concerns a Water Absorbent Resin Composition Further Comprising a Plant Component (C).

Further, this invention concerns an absorbent material for sanitary products comprising the water-absorbent resin compositions mentioned above, and hydrophilic fibers.

This invention further concerns an absorbent material for sanitary product comprising: water-absorbent resin obtainable by polymerizing an unsaturated monomer containing an acid group and/or a salt thereof, hydrophilic fiber; and complex oxide hydrate containing zinc and silicon, or zinc and aluminum, wherein the complex oxide hydrate contains zinc as main metal component, the mass ratio of the content of zinc and the content of silicon or aluminum is in the range of 50/50-99/1, and the water-absorbent resin has the absorption capacity at 60 minutes toward 0.90 mass % sodium chloride aqueous solution under the pressure of 1.9 kPa not less than 20 g/g, This invention concerns an absorbent product comprising the absorbent material mentioned above, topsheet possessing permeability to liquid; and backsheet possessing impermeability to liquid.

This invention also concerns a method for producing water-absorbent resin composition comprising the steps of: polymerizing an unsaturated monomer containing an acid group thereby obtaining a water-absorbent resin having not less than 20 g/g of absorption capacity at 60 minutes toward 0.90 mass % sodium chloride aqueous solution under the pressure of 1.9 kPa; and mixing the water-absorbent resin and complex oxide hydrate containing zinc and silicon, or zinc and aluminum.

The water-absorbent resin composition, the absorbent material, and the absorbent product of this invention suffer only a low ratio of separation of additives from water-absorbent resin, excel in hygroscopic and fluid property and deodorizing property, and excel also in gel strength and absorbing property. By the method of production according to this invention, the water-absorbent resin composition possessing such characteristics can be obtained.

DETAILED DESCRIPTION OF THE INVENTION (1) Water-Absorbent Resin (A)

The term "absorbent resin" (A) as used in this invention refers to a cross-linked polymer which is capable of forming a hydrogel and manifesting water-swelling property and water insolubility. The term "water-swelling property" refers to the ability of the water-absorbent resin in deionized water to absorb the water in a large amount of not less than 5 times, preferably 50 times to 1000 times, its own weight. The term "water insolubility" refers to the fact that the content of the uncross-linked water-soluble component (water-soluble polymer) in the water-absorbent resin (A) is preferably not more than 50 mass % (lower limit: 0 mass %), more preferably not more than 25 mass %, still more preferably not more than 20 mass %, and particularly preferably not more than 15 mass %, and most preferably not more than 10 mass %. Incidentally, the method for determining this water-soluble component is described in Edana Recommended Test Methods 470, 1-99 Etractables of European Disposables and Nonwovens Association.

When the content ratio based on the water-absorbent resin in is mentioned in the description of the invention, it is based on the solids content of the water-absorbent resin. It is calculated as the content ratio which is obtained, for example, by drying 1 g of water-absorbent resin for three hours so as to lower the water content thereof to not more than 10 mass %.

As the water-absorbent resin (A) in this invention, the water-absorbent resin which results from polymerizing an unsaturated monomer containing an acid group and/or a salt thereof and possesses a cross-linked structure is used from the viewpoint of deodorizing property and absorbent property.

As the water-absorbent resin (A), one or more compounds selected from the group consisting of partially neutralized polymer of polyacrylic acid; hydrolyzate of starch-acrylonitrile graft polymer; starch-acrylic acid graft polymer; saponified vinyl acetate-acrylic ester copolymer; hydrolyzate of acrylonitrile copolymer or acrylamide copolymer or cross-linked product thereof; modified carboxyl group-containing cross-linked polyvinyl alcohol; and cross-linked isobutylene-maleic anhydride copolymer may be used. Preferably, as the water-absorbent resin (A), the partially neutralized polymer of polyacrylic acid which is obtained by polymerizing and cross-linking a monomer component having acrylic acid and/or a salt (product of neutralization) thereof as a main component is used.

The water-absorbent resin (A) possesses an acid group and/or a salt thereof. Preferably, the water-absorbent resin (A) is obtained by polymerizing a monomer component having an acid group-containing unsaturated monomer as a main component. The acid group-containing unsaturated monomer includes such a monomer as acrylonitrile which is transformed into an acid group by undergoing hydrolysis subsequent to polymerization. Preferably, the acid group-containing unsaturated monomer which contains the acid group during the course of polymerization is used.

In this invention, the monomer component is preferred to have acrylic acid and/or a salt thereof as a main component.

When the monomer component has acrylic acid and/or a salt thereof as a main component, it may use other monomer in combination therewith. The monomer to be used in this combination does not need to be particularly restricted but is only required to ensure manifestation of the effect of this invention. As concrete examples of the monomer useful for this purpose, such water-soluble or hydrophobic unsaturated monomers as methacrylic acid, maleic acid, maleic anhydride, fumaric acid, crotonic acid, itaconic acid, vinyl sulfonic acid, 2-(meth)acrylamide-2-methylpropane sulfonic acid, (meth)acryloxyalkane sulfonic acid, and alkali metal salts thereof, and ammonium salts, N-vinyl-2-pyrrolidone, N-vinyl acetamide, (meth)acrylamide, N-isopropyl (meth) acrylamide, N,N-dimethyl(meth)acrylamide, 2-hydroxyethyl(meth)acrylate, methoxypolyethylene glycol (meth) acrylate, polyethylene glycol (meth)acrylate, isobutylene, and lauryl (meth)acrylate may be cited.

When a monomer other than acrylic acid and/or a salt thereof is used, the ratio of the monomer other than acrylic acid and/or the salt thereof is preferably 0-30 mol % and more preferably 0-10 mol % based on the total amount of the acrylic acid and/or the salt thereof. By using the monomer in this ratio, the performance of absorption of the produced water-absorbent resin is further enhanced. The use of this monomer allows the water-absorbent resin to be obtained more inexpensively. Further, the effect of this invention can be manifested satisfactorily.

The water-absorbent resin (A) possesses a cross-linked structure. The cross-linked structure may be a self-cross-linked type using no cross-linking agent. Preferably, the water-absorbent resin (A) possesses a cross-linked structure which is formed by the copolymerization or reaction using an inner cross-linking agent possessing two or more polymerizing unsaturated groups or two or more reactive groups within the molecular unit.

As concrete examples of the inner cross-linking agent, N,N'-methylenebis(meth)acrylamide, (poly)ethylene glycol di(meth)acrylate, (poly)propylene glycol di(meth)acrylate, trimethylol propane tri(meth)acrylate, glycerin tri(meth) acrylate, glycerin acrylate methacrylate, ethylene oxide-modified trimethylol propane tri(meth)acrylate, pentaerythritol hexa (meth)acrylate, triallyl cyanurate, triallyl isocyanurate, triallyl phosphate, triallyl amine, poly(meth) allyloxy alkane, (poly)ethylene glycol diglycidyl ether, glycerol diglycidyl ether, ethylene glycol, polyethylene glycol, propylene glycol, glycerin, pentaerythritol, ethylene diamine, ethylene carbonate, propylene carbonate, polyethylene imine, and glycidyl (meth)acrylate may be cited.

The inner cross-linking agents may be used either singly or in the form of a proper mixture of two or more members. The inner cross-linking agents may be added collectively at once or piecemeal to the reaction system. When the inner cross-linking agent is used, it is favorable to use a compound possessing two or more polymerizing unsaturated group during polymerization for the purpose of enabling the effect of this invention to be fully manifested.

The amount of the inner cross-linking agent to be used is preferably in the range of 0.001-2 mol %, more preferably 0.005-0.5 mol %, still more preferably 0.01-0.2 mol %, and particularly preferably 0.03-0.15 mol % based on the amount of the monomer component excluding the cross-linking agent. If the amount of the inner cross-linking agent to be used falls short of 0.001 mol % or exceeds 2 mol %, the deviation from the limits may possibly prevent the produced water-absorbent resin from manifesting the absorbent property fully satisfactorily. It may also possibly prevent the effect of this invention from being fully manifested.

The introduction of the cross-linked structure into the polymer by the use of the inner cross-linking agent may be accomplished by adding the inner cross-linking agent to the reaction system before, during, or after the polymerization of the monomer component or after the neutralization thereof.

Though neutralizing ratio of the water-absorbent resin (A) used in the present invention is not particularly restricted, the neutralizing ratio is preferably 30-90 mol %, more preferably 30-75 mol %, still more preferably 30-70 mol %, most preferably not less than 50 mol % and less than 70 mol % for the sake of enabling the effect of this invention to be satisfactorily manifested.

As means to polymerize the monomer component for the purpose of obtaining the water-absorbent resin (A), aqueous solution polymerization, reversed-phase suspended polymerization, bulk polymerization, and precipitation polymerization, for example, are available. From the viewpoint of such factors as the performance, the ease of control of the polymerization, and the absorbent property of the swelled gel, the aqueous solution polymerization or the reversed-phase suspended polymerization performed in an aqueous solution containing the monomer component proves advantageous.

The concentration of the monomer component in the aqueous solution containing the monomer component (hereinafter occasionally referred to as "aqueous monomer solution") is not particularly restricted but may be decided by the temperature of the aqueous solution and the kind of the monomer component. The concentration of the monomer component is preferably in the range of 10-70 mass % and more preferably 20-60 mass %. When the aqueous solution polymerization is performed, a solvent other than water may be additionally used as occasion demands. The kind of solvent which is so used additionally is not particularly restricted.

The reversed-phase suspension polymerization is a method of polymerization which requires the aqueous monomer solution to be suspended in a hydrophobic organic solvent. The reversed-phase suspended polymerization is disclosed, for example, in U.S. Pat. No. 4,093,776, U.S. Pat. No. 4,367,323, U.S. Pat. No. 4,446,261, U.S. Pat. No. 4,683,274, and U.S. Pat. No. 5,244,735. The aqueous solution polymerization is a method of polymerizing the aqueous monomer solution without using a dispersing solvent. The aqueous solution polymerization is disclosed, for example, in such U. S. patents as U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, and U.S. Pat. No. 5,380,808 and such European patents as European Patent No. 0811636, European Patent No. 0955086, and European Patent No. 0922717. The monomer components and the initiating agents which are cited in these methods of polymerization may be adopted for the present invention.

In initiating the polymerization, such radical polymerization initiators as potassium persulfate, ammonium persulfate, sodium persulfate, t-butyl hydroperoxide, hydrogen peroxide, and 2,2'-azobis(2-amidinopropane) dihydrochloride; and such photopolymerization initiators as 2-hydroxy-2-methyl-1-phenyl-propan-1-on may be used. The amount of the polymerization initiator to be used is preferably in the range of 0.001-2 mol %, and more preferably 0.01-0.1 mol % based on the total monomer component in consideration of physical properties of the produced water-absorbent resin.

By performing the polymerization, generally a hydrogel type cross-linked polymer is obtained. This hydrogel type cross-linked polymer is optionally divided finely, and dried, then preferably pulverized before and/or after the drying to obtain the water-absorbent resin.

The drying is effected at a temperature preferably in the range of 60° C.-250° C., more preferably 100° C.-220° C., and still more preferably 120° C.-200° C. The drying time is selected, depending on the surface area and the water content of the polymer and the kind of the drying device, so as to control a target water content of the water-absorbent resin.

The water content of the water-absorbent resin (A) is not particularly restricted. For the purpose of ensuring the effect of this invention to be manifested satisfactorily, the water-absorbent resin (A) is preferred to be in the form of a powder capable of manifesting fluidity even at room temperature. The water content of the water-absorbent resin (A) is preferably 0.2-30 mass %, more preferably 0.3-15 mass %, and still more preferably 0.5-10 mass %. The water-absorbent resin (A) is preferably in the form of powder. The water content of the water-absorbent resin is determined as the amount of water contained in the water-absorbent resin. It is determined, for example, as the amount of loss to be found by drying 1 g of a given water-absorbent resin at 180° C. for three hours.

Since it is difficult to decrease to zero the water content of the water-absorbent resin, it is permissible to use the water-absorbent resin in the form of powder which contains a small amount of water on the order of 0.5-10 mass %. When the properties specified in the present specification are determined with respect to the water-absorbent resin and the water-absorbent resin composition which are commercially available or the water-absorbent resin and the water-absorbent resin composition which are actually used in disposable diapers, they are determined after a given sample has been dried till the water content decreases to not more than 10 mass % or it is preferably adjusted to 5±2 mass %. The drying conditions for the sake of adjusting the water content do not need to be particularly restricted but are only required to avoid inducing the water-absorbent resin or the water-absorbent resin composition to sustain any decomposition or denaturation. Preferably, the drying may be performed under reduced pressure at the temperature of not more then 70° C.

The particulate shape of the water-absorbent resin (A) is not particularly restricted. The particulates of the water-absorbent resin (A) may assume the shape of spheres, crushed fragments, or amorphous grains, for example. The water-absorbent resin is preferred to be in the shape of amorphously crushed grains which are obtained through the pulverizing step. The bulk density of the water-absorbent resin (A) specified in JIS (Japanese Industrial Standard) K-3362, for the sake of enabling the effect of this invention to be satisfactorily manifested, is preferably in the range of 0.50-0.75 g/ml, and more preferably 0.60-0.73 g/ml.

The water-absorbent resin (A) which can be used in this invention is preferred to have further undergone a surface cross-linking (secondary cross-linking) treatment.

Various cross-linking (surface cross-linking) agents are available for the purpose of performing the surface cross-linking treatment and do not need to be particularly restricted. From the viewpoint of enhancing the properties of the produced water-absorbent resin, polyhydric alcohol compounds; epoxy compounds; polyamine compounds; and condensates thereof with haloepoxy compounds; oxazoline compounds; mono-, di-, and poly-oxazolidinone compounds; polyvalent metal salts; and alkylene carbonate compounds are advantageously used.

Though the surface cross-linking agent to be used does not need to be particularly restricted, such surface cross-linking agents as cited in U.S. Pat. No. 6,228,930, U.S. Pat. No. 6,071,976, and U.S. Pat. No. 6,254,990 are available. As concrete examples of the surface cross-linking agent, polyhydric alcohol compounds such as mono-, di-, tri-, tetra- or polyethylene glycol, monopropylene glycol, 1,3-propane diol, dipropylene glycol, 2,3,4-trimethyl-1,3-pentane diol, polypropylene glycol, glycerin, polyglycerin, 2-butene-1,4-diol, 1,4-butane diol, 1,3-butane diol, 1,5-pentane diol, 1,6-hexane diol, and 1,2-cyclohexane dimethanol; epoxy compounds such as ethylene glycol diglycidyl ether and glycidol; polyamine compounds such as ethylene diamine, diethylene triamine, triethylene tetramine, tetraethylene pentamine, pentaethylene hexamine, polyethylene imine, and polyamide polyamine; haloepoxy compounds such as epichlorohydrin, epibromohydrin, and α-methylepichlorohydrin; condensates of the polyamine compounds mentioned above and the haloepoxy compounds mentioned above; oxazolidinone compounds such as 2-oxazolidinone; and alkylene carbonate compounds such as ethylene carbonate may be cited. These surface cross-linking agents may be used either singly or in the form of a mixture of two or more members. For the purpose of ensuring the effect of this invention to be satisfactorily manifested, it is advantageous to use a polyhydric alcohol as the surface cross-linking agent. The polyhydric alcohol is preferred to be on the level of having 2-10 carbon atoms, preferably 3-8 carbon atoms.

The amount of the surface cross-linking agent to be used is preferably in the range of 0.001-10 mass %, and more preferably 0.01-5 mass %, based on the amount of the water-absorbent resin (A), though it is variable with the kinds of compound to be used and the combination thereof.

When the surface cross-linking is performed, it is preferable to use water. The amount of water to be used is preferably in the range of 0.5-20 mass %, and more preferably 0.5-10 mass %, based on the amount of the water-absorbent resin (A), though it depends on the water content of the water-absorbent resin (A) to be used. It is permissible to use a hydrophilic organic solvent besides water. When a hydrophilic organic solvent is used, the amount thereof is preferably in the range of 0-10 mass %, more preferably 0-5 mass %, and still more preferably 0-3 mass %, based on the amount of the water-absorbent resin (A).

The surface cross-linking is preferably effected by a method which comprises premixing water and/or a hydrophilic organic solvent and a surface cross-linking agent and subsequently causing the resultant aqueous solution to be mixed with the water-absorbent resin by spraying or dropwise addition. A method which resorts to spraying is adopted more preferably. The drops used for the spraying preferably have an average particle diameter in the range of 0.1-300 µm and more preferably 0.1-200 µm. When water and/or a hydrophilic organic solvent is mixed with the surface cross-linking agent, the mixture may be carried out in the presence of a water-insoluble fine powder or a surfactant on the condition that their existence does not obstruct the effect of this invention.

The water-absorbent resin which has been mixed with the surface cross-linking agent is preferably subjected to a heating treatment. The heating temperature which is determined as the thermal medium temperature or the material temperature is preferably in the range of 100-250° C. and more preferably 150-250° C. The heating time is preferably in the range of one minute to two hours. A preferred example of the combination of the heating temperature and the heating time is 0.1-1.5 hours at 180° C. and 0.1-1 hour at 200° C.

The preferably surface cross-linking water-absorbent resin which is produced by the procedure described above is preferably adjusted to a specific particle size distribution for the sake of ensuring the effect of this invention to be satisfactorily manifested. The adjustment of the particle size distribution may be performed either before or after the surface treatment. As the means for adjustment of the particle size distribution include, pulverization, classification, and granulation may be cited. It is preferable that these means are controlled to adjust the particle size distribution. Since the water-absorbent resin of this invention possesses such an acid group as carboxyl group and/or a salt thereof, it is capable of effectively neutralizing such a basic odorous substance as ammonia, for example. It appears that the surface area of the water-absorbent resin increases in proportion as the particle diameter decreases and the advantage in neutralizing the basic odorous substance increases in proportion as the surface area increases. It has been found, however, that in the actual use of a gelling agent for urine as in the disposable diaper, the water-absorbent resin as the gelling agent exhibits better results when it is controlled to a specific particle size distribution.

The mechanism responsible for the manifestation of the effect of adjusting the water-absorbent resin to a specific particle size distribution remains yet to be elucidated. It is inferred, however, that the gel state of the water-absorbent resin has some bearing on the effect in question. It is inferred that then the particle size distribution is unduly small, the water-absorbent resin induces the phenomenon of gel blocking on account of an unduly high speed of absorption of fluid and the fluid which has entrained an odorous component incurs difficulty in reaching the water-absorbent resin used or the water-absorbent resin composition containing the water-absorbent resin. When the particle size distribution of the water-absorbent resin is unduly large, the odorous component is volatilized from the fluid entraining it on account of an unduly small speed of absorption of the fluid.

To be more specific, the particles measuring not less than 150 μm and less than 850 μm preferably account for 90 mass % (upper limit: 100 mass %) or more of the whole particles and the particles measuring not less than 300 μm account for 60 mass % (upper limit: 100 mass %) or more of the whole particles. Preferably, the particles measuring not less than 150 μm and less than 850 μm is concluded more. Specifically, the particles measuring not less than 150 μm and less than 850 μm account for 95-100 mass % and more preferably 98-100 mass %. The particles measuring not less than 300 μm preferably account for not less than 65 mass %, more preferably not less than 70 mass %, and particularly preferably not less than 75 mass %. The upper limit for the particles measuring not less than 300 μm is not particularly restricted. Although the value is preferred to be higher, i.e. 100 mass %, the procedure to increase the value up to 100 mass % may possibly cause significant increase of production cost. From this viewpoint, the value may be not more than 99 mass %.

The mass average particle diameter of the water-absorbent resin (A) is preferably in the range of 200-700 μm, more preferably 300-600 μm, and particularly preferably 400-500 μm. The mass average particle diameter is applied also to the water-absorbent resin composition as described specifically herein below. The mass average particle diameter of the water-absorbent resin (A) or the water-absorbent resin composition may be adjusted, when necessary, by means of granulation.

The absorption capacity with 0.90 mass % of sodium chloride aqueous solution without load is preferably not less than 26 g/g, more preferably not less than 28 g/g, still more preferably not less than 30 g/g, and particularly preferably not less than 32 g/g. If the absorption capacity with 0.90 mass % of sodium chloride aqueous solution without load falls short of 26 g/g, the shortage will possibly result in preventing the effect of this invention from being manifested satisfactorily. Although the absorption capacity without load is preferred to be higher, the procedure to increase the absorption capacity without load more than a value may possibly cause significant increase of production cost and considerable decrease of other properties (e.g. the amount of the water-soluble component). From this viewpoint, the absorption capacity may be not more than 100 g/g, preferably not more than 90 g/g.

The absorption capacity with 0.90 mass % of sodium chloride aqueous solution under load of 1.9 kPa is preferably not less than 20 g/g, more preferably not less than 22 g/g, still more preferably not less than 24 g/g, and particularly preferably not less than 26 g/g. If the absorption capacity with 0.90 mass % of sodium chloride aqueous solution under load of 1.9 kPa falls short of 20 g/g, the shortage will possibly result in preventing the effect of this invention from being manifested satisfactorily. Although the absorption capacity under the pressure is preferred to be higher, the procedure to increase the absorption capacity under the pressure more than a value may possibly cause significant increase of production cost and considerable decrease of other properties. From this viewpoint, the absorption capacity may be not more than 60 g/g, preferably not more than 50 g/g.

For the purpose of enabling the effect of this invention to be manifested to the maximum, it is particularly advantageous to use a water-absorbent resin which has not less than 26 g/g of the absorption capacity with 0.90 mass % of sodium chloride aqueous solution without load and has not less than 20 g/g of the absorption capacity with 0.90 mass % of sodium chloride aqueous solution under the pressure of 1.9 kPa.

(2) Complex Oxide Hydrate (B)

The complex oxide hydrate (B) is a hydrate oxide which contains zinc as a main component based on the total mass of a metal component and contains (b1) zinc and silicon or (b2) zinc and aluminum. The ratio of the zinc element as a main component in the metal component is in the range of 50-99.9 mass %, preferably 60-95 mass %, and more preferably 70-95 mass %, based on the total metal component. The term "water-containing oxide," which is otherwise called a hydrated oxide, refers to the hydrate of a metal oxide including the so-called hydroxide. The complex oxide hydrate (B) in the case of (b1) is a water-containing oxide possessing the —Zn—O—Si-bond at least partly relative to zinc (Zn) and silicon (Si) and is different from the mere mixture of a water-containing oxide of Zn and a water-containing oxide of Si. By the same token, in the case of (b2), it is a water-containing oxide possessing the —Zn—O—Al-bond at least partly relative to zinc (Zn) and aluminum (Al) and is different from the mere mixture of water-containing oxide of Zn and water-containing oxide of Al. That is, the complex oxide hydrate (B) contains (b1) zinc and silicon or (b2) zinc and aluminum. For example, zeolite, the simple mixture of zinc oxide and silicon dioxide, and the simple mixture of zinc oxide and aluminum oxide are not included in the concept of the complex oxide hydrate (B). These compounds are liable to exfoliate from the surface of a water-absorbent resin. They do not lend themselves to the manifestation of the effect of this invention.

When the complex oxide hydrate (B) containing (b1) zinc and silicon or (b2) zinc and aluminum is present in the surface of the water-absorbent resin, the gel which the water-absorbent resin forms by absorbing an aqueous fluid does not easily separate or exfoliate from the surface of the water-absorbent resin. This behavior may be ascribable probably to the fact that the complex oxide hydrate of this invention which contains (b1) zinc and silicon or (b2) zinc and aluminum has a high mass ratio of zinc content in the metal component. In the case of a complex oxide hydrate containing titanium and aluminum or titanium silicon as cited, for example, in a comparative example described specifically herein below, when the water-absorbent resin is gelled by absorbing an aqueous fluid, the gel is easily separated or exfoliated from the surface of the water-absorbent resin. In the actual application of the water-absorbent resin to a disposable diaper, for example, for the sake of heightening the deodorizing effect, the separation or exfoliation of the gel from the surface of the water-absorbent resin is preferred to be as small as permissible.

Further, the complex oxide hydrate (B) which contains (b1) zinc and silicon or (b2) zinc and aluminum is more effective than the simple mixture of the oxides of the relevant metal elements. It is inferred that since the different metals of zinc and silicon or zinc and aluminum are present in close mutual proximity, the complex oxide hydrate (B) is enabled to repress its separation from the swelled gel and exalt the deodorizing effect more effectively than the mere mixture of the oxides of the relevant metal elements. When the water-absorbent resin composition of this invention is obtained by mixing the water-absorbent resin in a powdery form and the complex oxide hydrate in a powdery form, the complex oxide hydrate uniformly adheres to the surface of the water-absorbent resin and represses conspicuously such separation as is observed in the simple mixture.

When the complex oxide hydrate (B) contains (b1) zinc and silicon or (b2) zinc and aluminum at a mass ratio contemplated by this invention as described specifically herein below, it may contain other metal component. From the viewpoint of enhancing the effect further and in terms of the expense, however, the complex oxide hydrate (B) is preferred to be formed solely of the two kinds of metal, i.e. (b1) zinc and silicon or (b2) zinc and aluminum. When the complex oxide hydrate (B) has three or more metal components, the content of the third metal component is preferred to be not more than 5 mass %, more preferably not more than 3 mass %, and still more preferably not more than 1 mass %, based on the total metal components. When zinc is an essential main component in the metal components, the complex oxide hydrate (B) may contain magnesium, calcium, silver, copper, nickel, iron, manganese, titanium, barium, and zirconium.

The mass ratio of the content of zinc and the content of silicon in the complex oxide hydrate (B) containing (b1) zinc and silicon is preferred to be in the range of 50/50-99/1, more preferably 60/40-99/1, still more preferably 65/35-95/5, and particularly preferably 70/30-95/5. If the mass ratio deviates from the range mentioned above, the deviation will possibly result in preventing the effect of this invention to be manifested satisfactorily.

The mass ratio of the content of zinc and the content of aluminum in the complex oxide hydrate (B) containing (b2) zinc and aluminum is preferred to be in the range of 50/50-99/1, more preferably 60/40-99/1, still more preferably 65/35-95/5, and particularly preferably 70/30-95/5. If the mass ratio deviates from the range mentioned above, the deviation will possibly result in preventing the effect of this invention to be manifested satisfactorily.

When the mass ratio of the contents of the metal components in the complex oxide hydrate (B) containing (b1) zinc and silicon or (b2) zinc and aluminum is not known, it may be measured by such methods as fluorescent X-ray analysis and elementary analysis, for example.

The complex oxide hydrate (B) which contains (b1) zinc and silicon or (b2) zinc and aluminum is allowed to contain oxygen as a main component relative to the total mass of nonmetallic components. Hydrogen may be included in other nonmetallic components. Such impure components as the by-product of reaction may be contained in a trace quantity. The ratio of the oxygen element as the main component in the nonmetallic components is generally in the range of 50 mass %-99.9 mass %, preferably 60-95 mass %, and more preferably 70-95 mass % in the total metal element components.

The content of the complex oxide hydrate (B) containing (b1) zinc and silicon or (b2) zinc and aluminum is preferably in the range of 0.001-5 parts by weight, more preferably 0.05-4 parts by weight, and still more preferably 0.1-3 parts by weight, based on 100 parts by weight of the water-absorbent resin (A). If the content falls short of 0.001 parts by weight, the shortage will possibly result in preventing the deodorizing property from being manifested satisfactorily. If this content exceeds 5 parts by weight, the excess will possibly result in degrading the absorbent property inherent in the water-absorbent resin.

The particle diameter of the complex oxide hydrate (B) containing (b1) zinc and silicon or (b2) zinc and aluminum is preferably in the range of 0.001-1000 μm, and more preferably 0.01-600 μm. The mass average particle diameter is preferably not more than 500 μm and more preferably not more than 300 μm.

The complex oxide hydrate (B) containing (b1) zinc and silicon or (b2) zinc and aluminum is preferred to be obtained by a specific method. Although the complex oxide hydrate (B) containing (b1) zinc and silicon or (b2) zinc and aluminum can be obtained by various methods such as liquid phase method, gas phase method, and solid phase method, from the viewpoint of the equipment and the cost of production, it is manufactured preferably by a liquid phase method and more preferably by a co-precipitation method. Generally, the term "co-precipitation method" means a procedure of causing two or more species of ions to precipitate simultaneously. In this invention, the co-precipitate of a prescribed composition is obtained by the co-precipitation method, i.e. by varying the concentration, pH, temperature, and solvent of the mixed solution containing two or more species of ions thereby inducing simultaneous co-precipitation of the two or more species of ions. Then, by separating the co-precipitate and drying, the target compound is obtained. The co-precipitation method differs from the method which comprises forming precipitates separately of individual metals, separating the precipitates, drying the separated precipitates thereby obtaining powders respectively, and simply mixing the powders.

In the production of the complex oxide hydrate (B) containing (b1) zinc and silicon or (b2) zinc and aluminum by the co-precipitation method, the method for inducing the co-precipitation does not need to be particularly restricted but may be selected from among various methods which are available. A method which comprises adding aqueous ammonia and urea to the mixed solution containing a salt of zinc and a salt of silicon or the mixed solution containing a salt of zinc and a salt of aluminum and optionally heating the resultant mixture; and a method which comprises adding an aqueous ammonia and urea to the mixed solution containing a salt of zinc and a salt of aluminum and optionally heating the resultant mixture may be cited as concrete examples of the method.

The examples of the salts of zinc, the salts of silicon, and the salts of aluminum are not particularly restricted. The sulfates, oxysulfates, chlorides, oxychlorides, nitrates, oxynitrates, and carboxylates of zinc, silicon, and aluminum may be cited as concrete examples. Among these salts cited above, sulfates, oxysulfates, chlorides, and oxychlorides are used particularly advantageously.

As a means to initiate the precipitation, a method for inducing co-precipitation by simultaneous hydrolysis from a mixed solution containing an alkoxide of zinc and an alkoxide of silicon; and a method for inducing co-precipitation by simultaneous hydrolysis from a mixed solution containing an alkoxide of zinc and an alkoxide of aluminum are advantageously used besides a method which uses a salt as a raw material. The examples of alkoxide of zinc, alkoxide of silicon, and alkoxide of aluminum are not particularly discriminated. Methoxides, ethoxides, propoxides, and butoxides of zinc, silicon, and aluminum may be cited as concrete examples.

The precipitating conditions during the initiation of co-precipitation are important, in exerting an influence on the speed of precipitation and the shape of a co-precipitate to be produced. Since they are varied by the composition and concentration of the mixed solution, the kind of a precipitating substance, the method for initiating the precipitation, and the like, they ought to be properly selected to suit such factors.

The co-precipitate which is formed by the co-precipitation is optionally filtered, washed, and then dried. The drying temperature used in this case is preferred to be comparatively low. It is preferred to be in the range of 100° C.-200° C. If the drying temperature exceeds 600° C., this unduly high temperature will possibly result in degrading the deodorizing property of the product.

(3) Plant Component (C)

As the plant component (C), at least one compound selected from the group consisting of polyphenols, flavones and the likes thereof, and caffeines, is contained in a proportion exceeding 0 and not exceeding 100 mass % based on the total mass of the plant component (C). Preferably, at least one compound selected from among tannins, tannic acid, gall, nutgall, and gallic acid is used as the plant component (C).

As concrete examples of the plants containing the plant component (C), the theaceous plants such as camellia, eurya, and termstroemia, the gramineae plants such as rice, bamboo grass, bamboo, corn, and wheat, and the plants of family rubiaceae such as coffee may be cited.

As concrete examples of the form of the plant component (C), the extracts (essential oil) drawn from plants, the plants themselves (plant powder), and plants lees and extraction lees by-produced during the production processes in the plant processing industry and the food processing industry may be cited, though not exclusively.

The amount of the plant component (C) to be used is variable with the deodorizing function aimed at. It is preferably in the range of 0.001-10 parts by weight and more preferably 0.01-5 parts by weight based on 100 parts by weight of the water-absorbent resin (A). If this amount falls short of 0.001 parts by weight, the shortage will possibly result in preventing the effect from being satisfactorily manifested. If the amount exceeds 10 parts by weight, the excess will possibly fail to bring proportionate addition to the effect.

When the plant component (C) is in the form of a powder solely; and/or when the plant component (C) is in the form of a powder having deposited thereon an extract (essential oil) drawn from a plant and containing a plant component (C); and/or when the plant component (C) is in the form of a powder having an extract (essential oil) drawn from a plant and containing a plant component (C) deposited on an impalpable powder (B) formed of an aggregate of a metal hydrate oxide containing zinc and silicon or zinc and aluminum, the particle diameters of not less than 90 mass % of the particles are preferably in the range of 0.001-1000 µm and more preferably 0.01-600 µm. The mass average particle diameters are preferably not more than 500 µm and more preferably not more than 300 µm. If the mass average particle diameters exceed 500 µm, the excess will possibly render impartation of a stable deodorizing property impossible because the particles, on contacting urine, prevent the effective component contained in the plant component (C) from functioning satisfactorily. The fact that the mass average particle diameter of the powder containing the plant component (C) is smaller than the mass average particle diameter of the water-absorbent resin is at an advantage in being able to impart good deodorizing property and stability to the water-absorbent resin.

The plant component (C) is preferred to be a liquid and/or an aqueous solution at room temperature.

(4) Water-Absorbent Resin Composition

The water-absorbent resin composition of this invention comprises the aforementioned water-absorbent resin (A) and the complex oxide hydrate (B) containing (b1) zinc and silicon or (b2) zinc and aluminum. That is, the water-absorbent resin composition of this invention is a water-absorbent resin composition which contains a water-absorbent resin (A) obtained by polymerizing an unsaturated monomer containing an acid group and/or a salt thereof and a complex oxide hydrate (B) containing (b1) zinc and silicon or (b2) zinc and aluminum.

The mass ratio of the contents of zinc and silicon or the mass ratio of the contents of zinc and aluminum in the complex oxide hydrate (B) containing (b1) zinc and silicon or (b2) zinc and aluminum is preferably in the range of 50/50-99/1, more preferably 60/40-99/1, still more preferably 65/35-90/10, and particularly preferably 70/30-90/10. When a complex oxide hydrate containing the three components, i.e. zinc, silicon, and aluminum, is used, the aforementioned mass ratio is preferred to be satisfied with respect to at least one of them and the aforementioned mass ratio is preferred to be satisfied with respect to both of them. When the mass ratio of zinc to silicone or the mass ratio of zinc to aluminum is in the range of 1/99-49/52 in the complex oxide hydrate (B) containing zinc and silicon or zinc and aluminum, the deodorizing property capable of removing satisfactorily the offensive odor originating such a sulfur type compound as hydrogen sulfide and mercaptans cannot be manifested.

The method for producing the water-absorbent resin composition is not particularly restricted. The method preferably comprises the steps of polymerizing an unsaturated monomer containing an acid group thereby obtaining a water-absorbent resin; and mixing the water-absorbent resin and a complex oxide hydrate containing zinc and silicon or zinc and aluminum. By this method, a water-absorbent resin composition having not less than 20 g/g of absorption capacity (value at 60 minutes) toward 0.90 mass % of sodium chloride aqueous solution under the pressure of 1.9 kPa can be obtained.

The expression "the water-absorbent resin" (A), which can be obtained via a polymerizing step, means a water-absorbent resin which has completed undergoing a polymerization step. It embraces a water-absorbent resin which is obtained by polymerization and not given a surface cross-linking treatment and a water-absorbent resin which is given a surface cross-linking treatment after polymerization.

The polymerizing step of polymerizing a monomer component having an acid group-containing unsaturated monomer as a main component and consequently obtaining a water-absorbent resin (A) has been already described.

The absorption capacity of the water-absorbent resin (A) obtained via the polymerizing step toward 0.90 mass % of sodium chloride aqueous solution without load is preferred to be not less than 26 g/g, more preferably not less than 28 g/g, still more preferably not less than 30 g/g, and particularly preferably not less than 32 g/g. If the absorption capacity toward the 0.90 mass % sodium chloride aqueous solution without load falls short of 26 g/g, the shortage will possibly result in preventing the effect of this invention from being manifested satisfactorily. Although the absorption capacity without load is preferred to be higher, the procedure to increase the absorption capacity without load more than a value may possibly cause significant increase of production cost and considerable decrease of other properties (e.g. the amount of the water-soluble component). From this viewpoint, the absorption capacity may be not more than 100 g/g, preferably not more than 90 g/g.

The absorption capacity of the water-absorbent resin (A) obtained via the polymerizing step toward the 0.90 mass % sodium chloride aqueous solution under the pressure of 1.9 kPa is preferably not less than 20 g/g, more preferably not less than 24 g/g, still more preferably not less than 26 g/g, and particularly preferably not less than 28 g/g. If the absorption capacity toward the 0.90 mass % sodium chloride aqueous solution under the pressure of 1.9 kPa falls short of 20 g/g, the shortage will possibly prevent the effect of this invention to be satisfactorily manifested. Although the absorption capacity under the pressure is preferred to be higher, the procedure to increase the absorption capacity under the pressure more than a value may possibly cause significant increase of production cost and considerable decrease of other properties. From this viewpoint, the absorption capacity under the pressure may be not more than 60 g/g, preferably not more than 50 g/g.

For the sake of enabling the effect of this invention to be manifested to the maximum, the water-absorbent resin (A) obtained via the polymerizing step particularly preferably has an absorption capacity of not less than 26 g/g toward the 0.90 mass % sodium chloride aqueous solution without load and an absorption capacity of not less than 20 g/g toward the 0.90 mass % sodium chloride aqueous solution under the pressure of 1.9 kPa.

The complex oxide hydrate (B) containing (b1) zinc and silicon or (b2) zinc and aluminum is preferred to be added to the water-absorbent resin (A) which has been obtained via the polymerizing step. Owing to the addition of the complex oxide hydrate (B) to the water-absorbent resin (A) obtained via the polymerizing step, the complex oxide hydrate (B) containing (b1) zinc and silicon or (b2) zinc and aluminum is made to occur dominantly on the surface of the water-absorbent resin (A) and the effect of this invention is consequently manifested more satisfactorily. Though the manner of adding the complex oxide hydrate (B) to the water-absorbent resin obtained via the polymerizing step does not need to be particularly discriminated, the embodiment of making the addition after polymerization and drying, the embodiment of performing the addition during the course of the surface cross-linking treatment, and the embodiment of effecting the addition during the course of granulation may be cited as concrete examples of the addition. Incidentally, the complex oxide hydrate (B) containing (b1) zinc and silicon or (b2) zinc and aluminum may be added not only to the water-absorbent resin (A) obtained subsequent to polymerization but also to the monomer component prior to polymerization and to the reactants during the course of the polymerization.

The amount of the complex oxide hydrate (B) containing (b1) zinc and silicon or (b2) zinc and aluminum to be added is preferably in the range of 0.001-5 parts by weight, more preferably 0.05-4 parts by weight, and still more preferably 0.1-3 parts by weight based on 100 parts by weight of the water-absorbent resin (A). If the amount of this addition falls short of 0.001 parts by weight, the shortage will possibly render deficient the deodorizing property of removing the offensive odor arising from such sulfur type compounds as hydrogen sulfide and mercaptans. If the amount exceeds 5 parts by weight, the excess will possibly result in degrading the absorbent property inherent in the water-absorbent resin.

As concrete examples of the procedure of the addition of the complex oxide hydrate (B) to the water-absorbent resin (A) obtained via the polymerizing step, a method of directly mixing the complex oxide hydrate (B) with the water-absorbent resin so as to ensure addition in a prescribed amount (the dry blend method when the two components are both powders); a method of mixing water, an aqueous liquid, or a various organic solvent by spraying or dropwise addition with what is obtained by directly mixing into the water-absorbent resin by the method just mentioned; and a method of dispersing such additives in an aqueous liquid or a various organic solvent thereby forming a slurry and adding the slurry to the water-absorbent resin may be cited. When the additives are mixed with the aqueous liquid or various organic solvent, the resultant mixture may be dried as occasion demands.

When the water-absorbent resin and the complex oxide hydrate (B) containing (b1) zinc and silicon or (b2) zinc and aluminum are mixed, the optimum amount of water, steam, an aqueous solution of a hydrophilic organic solvent, or a various organic solvent to be optionally added is variable with the kind and the particle size distribution of the water-absorbent resin (A). When water is used, the optimum amount of addition is preferably not more than 10 mass % and more preferably falling in the range of 1-5 mass %, based on the mass of the water-absorbent resin (A). When a hydrophilic organic solvent is used, the amount of addition is preferably not more than 10 mass % and more preferably falling in the range of 0.1-5 mass %, based on the mass of the water-absorbent resin (A).

The device to be used when the water-absorbent resin and the complex oxide hydrate (B) containing (b1) zinc and silicon or (b2) zinc and aluminum are mixed may be any of the various ordinary devices available for the purpose of mixture. As concrete examples of the device, cylindrical mixers, screw type mixers, screw type extruders, high-speed stirrer type mixers (for example, turbulizers), Nautar type mixer, V shaped mixers, ribbon type mixers, twin-arm type kneaders, fluid type mixers, pneumatic conveyor mixers, rotary disc type mixers, roll mixers, rolling type mixers, and spade-shaped shovel vane mixers (for example, Redige mixer) may be cited. The speed of this mixing may be high or low.

The method of producing the water-absorbent resin composition of this invention may additionally incorporate therein a step of adding deodorant, antibacterial agent, perfume, foaming agent, pigment, dye, plasticizer, tackifier, surfactant, fertilizer, oxidizing agent, reducing agent, water, salt, chelating agent, fungicide, hydrophilic polymer such as polyethylene glycol or polyethylene imine, hydrophobic polymer such as paraffin, thermoplastic resin such as polyethylene or polypropylene, and thermosetting resin such as polyester resin or urea resin. These additives are added in a proportion preferably in the range of 0-30 mass %, more preferably 0-20 mass %, and still more preferably 0-10 mass % based on the mass of the water-absorbent resin.

The content of the water-absorbent resin in the water-absorbent resin composition is not particularly restricted. For the sake of ensuring the effect of this invention to be satisfactorily manifested, the content is preferably in the range of 70-99 mass %, more preferably 80-99 mass %, and particularly preferably 90-99 mass %.

The water-absorbent resin composition of the present invention may further contain various inorganic powder, if necessary. As concrete example of the inorganic powder, metal oxide such as silicone dioxide and titanium oxide; silicic acid (silicate) such as natural zeolite and synthetic zeolite; kaoline, talc, clay, bentonite can be cited.

The absorption capacity of the water-absorbent resin composition of this invention toward the 0.90 mass % sodium chloride aqueous solution without load is preferably not less than 26 g/g, more preferably not less than 28 g/g, still more preferably not less than 30 g/g, and particularly preferably not less than 32 g/g. If the absorption capacity toward the 0.90 mass % sodium chloride aqueous solution without load falls short of 26 g/g, the shortage will possibly prevent the effect of this invention from being satisfactorily manifested. Although the absorption capacity without load is preferred to be higher, the procedure to increase the absorption capacity without load more than a value may possibly cause significant increase of production cost and considerable decrease of other properties (e.g. the amount of the water-soluble component). From this viewpoint, the absorption capacity may be not more than 100 g/g, preferably not more than 90 g/g.

The absorption capacity of the water-absorbent resin composition of this invention toward the 0.90 mass % sodium chloride aqueous solution under the pressure of 1.9 kPa is preferably not less than 20 g/g, more preferably not less than 24 g/g, still more preferably not less than 26 g/g, and particularly preferably not less than 28 g/g. If the absorption capacity toward the 0.90 mass % sodium chloride aqueous solution under the pressure of 1.9 kPa falls short of 20 g/g, the shortage will possibly prevent the effect of this invention from being satisfactorily manifested. Although the absorption capacity under the pressure is preferred to be higher, the procedure to increase the absorption capacity under the pressure more than a value may possibly cause significant increase of production cost and considerable decrease of other properties. From this viewpoint, the absorption capacity under the pressure may be not more than 60 g/g, preferably not more than 50 g/g.

For the sake of enabling the effect of this invention to be manifested to the maximum, it is particularly preferable that the water-absorbent resin composition of this invention possesses not less than 26 g/g of an absorption capacity toward the 0.90 mass % sodium chloride aqueous solution without load and not less than 20 g/g of an absorption capacity toward the 0.90 mass % sodium chloride aqueous solution under the pressure of 1.9 kPa. Owing to the possession of such a specific excellent absorption property by the water-absorbent resin composition of this invention, the deodorizing ability which is one of the effects of this invention can be manifested more satisfactorily.

The shape of the water-absorbent resin composition is not particularly restricted. Spheres, an aggregate of beads, and an amorphously crushed powder (particles) may be cited as concrete examples of the shape. In view of the height of the fixing property to fibers, the amorphously crushed powder (particles) is preferably adopted. For the sake of ensuring the effect of this invention to be satisfactorily manifested, the bulk density specified in JIS K-3362 is preferably in the range of 0.40-0.80 g/ml, more preferably 0.50-0.75 g/ml, and more preferably 0.60-0.73 g/ml.

The water content of the water-absorbent resin composition is not particularly restricted. For the sake of ensuring the effect of this invention to be satisfactorily manifested, the water-absorbent resin composition is preferred to be a powder which exhibits fluidity even at room temperature. To be specific, the water content is preferably in the range of 0.2-30 mass %, more preferably 0.3-15 mass %, and still more preferably 0.5-10 mass %. The water content is specified as the amount of water contained in the water-absorbent resin composition. For example, it is calculated by using 1 g of a given water-absorbent resin and finding the amount lost by three hours' drying at 180° C.

The amount of the water-soluble component of the water-absorbent resin composition is not particularly restricted, but the value is preferred to be lower. For the sake of ensuring the effect of this invention to be satisfactorily manifested, it is preferred to be not more than 50 mass %, more preferably not more than 25 mass %, still more preferably not more than 20 mass %, particularly preferably not more than 15 mass %, and most preferably not more than 10 mass %. The lower limit for the amount of the water-soluble component is not particularly restricted. Although the amount of the water-soluble component is preferred to be lower, i.e. 0 mass %, the procedure to decrease the amount of the water-soluble component may possibly cause significant increase of production cost or considerable decrease of the absorption capacity. From this viewpoint, the amount of the water-soluble component may be not less than 0.1 mass %, preferably not less than 1 mass %.

The degree of discoloration of the water-absorbent resin composition, as expressed by the YI index (Yellow Index: refer to European Patent No. 942014 and European Patent No. 1108745), is preferably in the range of 0-15, more preferably 0-13, still more preferably 0-10, and most preferably 0-5. The amount of the residual monomer in the water-absorbent resin composition is preferably not more than 1000 ppm (lower limit: 0 ppm) and more preferably not more than 500 ppm (lower limit: 0 ppm).

As regards the particle size distribution of the water-absorbent resin composition, preferably the particles measuring less than 850 µm and not less than 150 µm account for not less than 90 mass % of all the particles and the particles measuring not less than 300 µm account for not less than 60 mass % of all the particles. Preferably, the particles measuring less than 850 µm and not less than 150 µm is concluded more. Specifically, the particles measuring less than 850 µm and not less than 150 µm account for preferably 95-100 mass % and more preferably 98-100 mass % of all the particles. Then, the particles measuring not less than 300 µm account for preferably not less than 65 mass %, more preferably not less than 70 mass %, and particularly preferably not less than 75 mass % of all the particles. The upper limit is not particularly restricted. Although the value is preferred to be higher, i.e. 100 mass %, the procedure to increase the value up to 100 mass % may possibly cause significant increase of production cost. From this viewpoint, the value may be not more than 99 mass %.

If the particles measuring not less than 300 μm account for less than 60 mass %, the shortage will possibly render the accomplishment of the deodorizing effect of this invention difficult. In spite of the fact that the surface area to be covered decreases in proportion as the particle diameter is increased, the deodorizing effect is enhanced incredibly in accordance as the particle diameter of the water-absorbent resin composition is enlarged and the specific surface area thereof is decreased.

The mass average particle diameter of the water-absorbent resin composition is preferably in the range of 200-700 μm, more preferably 300-600 μm, and particularly preferably 400-500 μm. The mass average particle diameter of the water-absorbent resin composition may be optionally adjusted by means of granulation, for example.

For the sake of enabling the water-absorbent resin composition to acquire a good deodorizing property in actual use, the amount of the hydrogen sulfide residue under wet after three hours is preferred to be lower. Specifically, the amount is preferably 0-5 ppm, more preferably 0-3 ppm, still more preferably 0-2 ppm, and particularly preferably 0-1 ppm. Further, the amount of the hydrogen sulfide residue under wet after one hour is preferably 0-7 ppm, more preferably 0-5 ppm, and particularly preferably 0-3 ppm. The amount of the hydrogen sulfide residue under wet after 30 minutes is preferred to be lower. Specifically, the amount is preferably 0-9 ppm, more preferably 0-7 ppm, and particularly preferably 0-5 ppm.

For the sake of enabling the water-absorbent resin composition of this invention to acquire a good deodorizing property in actual use, the amount of wet ammonia residue after 60 minutes is preferably 0-50 ppm, more preferably 0-40 ppm, and particularly preferably 0-30 ppm. The amount of wet ammonia residue after 30 minutes is preferably 0-100 ppm, more preferably 0-80 ppm, and particularly preferably 0-60 ppm. Further, the amount of wet ammonia residue after 10 minutes is preferably 0-300 ppm, more preferably 0-250 ppm, and particularly preferably 0-220 ppm. In the case the value falls out of the range, the deodorizing property may possibly be insufficient in actual use such as disposable diaper, and a user may possibly feel uncomfortable. By controlling the value of the water-absorbent resin composition within the above range, the property can be sufficient also in actual use such as disposable diaper.

The water-absorbent resin composition effectively manifests the deodorizing property because the complex oxide hydrate (B) containing (b1) zinc and silicon or (b2) zinc and aluminum possesses a low separation ratio (for details of the separation ratio, refer to the example section cited herein below). The separation ratio of the complex oxide hydrate (B) containing zinc and silicon or zinc and aluminum is preferred to be lower. Specifically, the separation ration of the complex oxide hydrate (B) is preferably 0-20%, more preferably 0-15%, still more preferably 0-10%, and particularly preferably 0-5%. If the separation ratio of the complex oxide hydrate (B) containing zinc and silicon or zinc and aluminum exceeds 20%, the excess will possibly prevent the deodorizing effect possessed by the complex oxide hydrate (B) containing zinc and silicon or zinc and aluminum from being manifested effectively because the water-absorbent resin and the complex oxide hydrate (B) containing zinc and silicon or zinc and aluminum are separated when the water-absorbent resin composition is swelled by absorbing a fluid such as urine.

The water-absorbent resin composition excels in the powder handling property because it has a low hygroscopic blocking ratio as described in the example section cited herein below. The hygroscopic blocking ratio is preferred to be lower. Specifically, the hygroscopic blocking ration is preferably 0-30 mass %, more preferably 0-20 mass %, still more preferably 0-10 mass %, and particularly preferably 0-5 mass %. If the hygroscopic blocking ratio exceeds 30 mass %, the excess will possibly entail such disadvantages as impairing the fluidity of powder during the production of disposable diaper, for example, and rendering the production of the disposable diaper difficult.

(5) Absorbent Material

The water-absorbent resin composition of this invention has the water-absorbent resin (A) as a main component and generally assumes the form of powder. The absorbent material is obtained by causing the powdery water-absorbent resin composition to be formed in conjunction with other arbitrary absorbent material. The shape of the absorbent material is not particularly restricted. Preferred shapes thereof include sheets (otherwise called webs), cylinders, films, and fibers. The absorbent material is particularly preferred to be in the shape of sheet. When the water-absorbent resin composition is obtained in the shape of a sheet, the sheet may be used directly as an absorbent material.

For the sake of manifesting the effect of this invention, the absorbent material contains the water-absorbent resin (A) possessing a cross-linked structure with an acid group and/or a salt thereof as a main component and contains the complex oxide hydrate (B) containing (b1) zinc and silicon or (b2) zinc and aluminum and hydrophilic fibers.

The hydrophilic fibers are not particularly restricted. As concrete examples of the hydrophilic fibers, ground wood pulp, cotton linters, cross-linked cellulose fibers, rayon, cotton, wool, acetate, and Vinylon™ may be cited. Preferably, products obtained by air-laiding these materials are used.

The absorbent material of this invention may be produced by using the water-absorbent resin composition described above and the hydrophilic fibers. It may be otherwise produced by using the water-absorbent resin (A) possessing the cross-linked structure with an acid group and/or a salt thereof, the complex oxide hydrate (B) containing (b1) zinc and silicon or (b2) zinc and aluminum, and the hydrophilic fibers.

When the absorbent material of this invention is an absorbent material which contains the water-absorbent resin composition and the hydrophilic fibers, the content of the water-absorbent resin composition based on the total mass of the water-absorbent resin composition and the hydrophilic fibers which is called the core concentration preferably falls in the range of 20-100 mass %, more preferably 25-90 mass %, and still more preferably 30-80 mass %. If the core concentration falls short of 20 mass %, the amount of the water-absorbent resin composition to be used is small, and the shortage will possibly render insufficient the impartation of the deodorizing property to the entire disposable diaper, for example.

When the absorbent material of this invention is produced from the water-absorbent resin composition and the hydrophilic fibers, the method for effecting this production is not particularly restricted. The absorbent material is produced, for example, by dry-mixing the water-absorbent resin composition and the hydrophilic fibers in a ratio calculated to fall in the range of the core concentration mentioned above by the use of a mixing device such as a mixer, forming the resultant mixture in the shape of a web by means of pneumatic webbing, and, if necessary, subsequently subjecting the web to compression molding. This absorbent material is preferred to be compressed to a density in the range of 0.001-0.50 g/cm$^3$ and a basis weight in the range of 0.01-0.20 g/cm$^2$.

When the absorbent material of this invention is produced by using the water-absorbent resin (A) or the water-absorbent resin composition, the complex oxide hydrate (B), and the hydrophilic fibers, the absorption capacity of the water-absorbent resin (A) toward the 0.90 mass % sodium chloride aqueous solution under the pressure of 1.9 kPa is preferred to be not less than 20 g/g. The mass ratio of zinc and silicon or zinc and aluminum in the complex oxide hydrate (B) is preferred to be in the range of 50/50-99/1. Further, the absorption capacity (value at 60 minutes) of the water-absorbent resin toward the 0.90 mass % sodium chloride aqueous solution under the pressure of 1.9 kPa is preferred to be in the aforementioned range. If the mass ratio of zinc and silicon or zinc and aluminum in the complex oxide hydrate (B) deviates from the range mentioned above, the deviation will possibly prevent the absorbent material from manifesting the effect of this invention sufficiently.

When the absorbing material of this invention is produced by using the water-absorbent resin (A), the complex oxide hydrate (B), and the hydrophilic fibers, the method for production is not particularly restricted. For example, a method of dry-mixing the water-absorbent resin (A), the complex oxide hydrate (B), and the hydrophilic fibers at a ratio calculated to form the core concentration mentioned above by the use of a mixing device such as a mixer; a method of having water, aqueous liquid, and various organic solvent mixed by spraying or dropwise addition with the product of the dry-mixing; and a method of mixing a slurry resulting from dispersing the complex oxide hydrate (B) in an aqueous liquid or a various organic solvent with the water-absorbent resin and the hydrophilic fibers at a ratio calculated to form the core concentration mentioned above by the use of a mixing device such as a mixer may be cited as concrete examples of the method available for the production.

(6) Absorbent Product

The absorbent product of this invention is furnished with the absorbent material of this invention described above, a liquid-permeable topsheet, and a liquid-impermeable backsheet.

The method of producing the absorbent product is not particularly restricted. The absorbent material is interposed between a liquid-permeable medium destined to function as the topsheet and a liquid impermeable medium destined to function as the backsheet. By optionally disposing an elastic member, a dispersing layer, and an adhesive tape, an absorbent product such as, for example, an adult disposable diaper or a sanitary napkin is produced.

The water-absorbent resin composition and the absorbent material of this invention can impart a deodorizing function to the absorbent product and continue to exhibit excellent deodorizing property and absorbent property for a long time. As concrete use, such sanitary material as adult disposable diaper, infant disposable diaper, sanitary napkin, and so-called incontinence pad may be cited, though not exclusively. The absorbent product of this invention enjoys the veritably outstanding deodorizing ability inherent in the water-absorbent resin composition and the absorbent material, prevents the re-wet of fluid significantly, and emits a conspicuous dry sensation. Further, it greatly alleviates the burden on the person wearing the product and on the person nursing the person using it.

EXAMPLES

Now, examples and comparative examples of this invention will be specifically explained below. This invention is not limited to the following examples. Incidentally, the various properties of the water-absorbent resin, water-absorbent resin composition, and absorbent product indicated herein below were determined by the following methods. All the electrical devices used in the examples were invariably operated under the conditions of 100 V and 60 Hz. Further, the water-absorbent resin, the water-absorbent resin composition, and the absorbent product were used under the conditions of 25° C.±2° C. and RH 50% unless otherwise specified.

(a) Absorption Capacity Toward the 0.90 Mass % Sodium Chloride Aqueous Solution (Physiological Saline) without Load A given water-absorbent resin (or water-absorbent resin composition) weighing 0.20 g was uniformly placed in a pouch (60 mm×60 mm) made of non-woven fabric and immersed in an 0.9 mass % sodium chloride aqueous solution (physiological saline) adjusted to a temperature of 25±2° C. for 60 minutes. After the immersion, the pouch was lifted from the solution, drained with a centrifugal separator at 250 G for three minutes, and weighed to find the mass W2 (g) of the pouch. The same procedure was repeated without using the water-absorbent resin (or water-absorbent resin composition) to find the mass W1 (g) of the pouch. The absorption capacity (g/g) was calculated in accordance with the following formula using the two masses, W1 and W2 determined above.

Absorption capacity (g/g) toward the 0.90 mass % sodium chloride aqueous solution (physiological saline) without load=[(Mass W2 (g)-mass W1 (g))/mass (g) of the water-absorbent resin (or water-absorbent resin composition)]−1

(b) Absorption Capacity Toward the 0.90 Mass % Sodium Chloride Aqueous Solution (Physiological Saline) Under the Pressure of 1.9 kPa A given water-absorbent resin (or water-absorbent resin composition) weighing 0.90 g was uniformly scattered on a 400-mesh wire sheet made of stainless steel (mesh size 38 µm) fused to the bottom cylindrical section of a plastic supporting cylinder having an inside diameter of 60 mm. A piston (cover plate) having an outside diameter of slightly smaller than 60 mm, producing no gap with the wall surface of the supporting cylinder, and offering no obstruction to its own vertical motion was mounted on the water-absorbent resin. The supporting cylinder, the water-absorbent resin (or water-absorbent resin composition), and the piston were weighed to determine the total mass W3 (g). The whole system of determination was completed by mounting on the piston a load adjusted to exert uniformly a load of 1.9 kPa inclusive of the piston to bear on the water-absorbent resin (or water-absorbent resin composition). A glass filter 90 mm in diameter and 5 mm in thickness was placed inside a petri dish 150 mm in diameter and 0.9 mass % sodium chloride aqueous solution (physiological saline) adjusted to 25±2° C. was added to the petri dish till it rose to the same level as the upper surface of the glass filter. One sheet of filter paper 9 cm in diameter (produced by Toyo Roshi K.K. and sold under product code of "No. 2") was mounted on the glass filter and left standing thereon till the surface was completely wetted, with the excess liquid removed from the petri dish.

The whole system of determination was mounted on the wet filter paper and the water-absorbent resin was enabled to absorb the liquid under the load. When the liquid level fell from the upper part of the glass filter, the liquid was replenished so as to retain the liquid level constant. After the elapse of one hour, the whole system of determination was lifted and the mass W4 (g) (the total mass of the supporting cylinder, the swelled water-absorbent resin (or water-absorbent resin composition), and the piston) remaining after the removal of the load was determined. The absorption capacity (g/g) toward the 0.90 mass % sodium chloride aqueous solution (physiological saline) under the pressure of 1.9 kPa was calculated in accordance with the following formula using the masses W3 and W4 determined above.

Absorption capacity (g/g) toward 0.90 mass % sodium chloride aqueous solution (physiological saline) under the pressure of 1.9 kPa=(Mass W4 (g)−mass W3 (g))/mass (g) of the water-absorbent resin (or water-absorbent resin composition)

(c) Mass Average Particle Diameter

A given water-absorbent resin (or water-absorbent resin composition) was passed through JIS standard sieves having apertures of 850 μm, 600 μm, 500 μm, 425 μm, 300 μm, 212 μm, 150 μm, 106 μm, and 75 μm and the residual percentages consequently found were plotted on a logarithmic probability paper. The mass average particle diameter (D50) of the water-absorbent resin was read from the paper.

The screening was carried out by charging the JIS standard sieves having apertures of 850 μm, 600 μm, 500 μm, 425 μm, 300 μm, 212 μm, 150 μm, 106 μm, and 75 μm (the Iida Testing Sieve; inside diameter 80 mm) with a given water-absorbent resin powder (or water-absorbent resin composition powder) weighing 10.00 g and shaking these sieves with a low-tap type sieve shaker (made by Iida Seisakusho K.K. and sold under the trademark designation of "ES-65 Type Sieve Shaker") for 10 minutes. The term "mass average particle diameter (D50)" used herein refers to the particle diameter of the standard sieve corresponding to 50 mass % of all the particles separated by the standard sieves of fixed apertures as described in U.S. Pat. No. 5,051,259, for example.

(d) Deodorizing Test (Rating of Water-Absorbent Resin or Water-Absorbent Resin Composition)

In a lidded polypropylene cup having an inner volume of 120 ml, 50 ml of human urine collected from 20 adults was placed and a sample weighing 2.0 g of each of the water-absorbent resin (or water-absorbent resin compositions) obtained in the examples and the comparative examples described herein below was placed in the urine to obtain a swelled gel. The human urine used herein was within two hours old from the time of excretion. The cup was lidded and the swelled gel was retained therein at 37° C. The lid was removed from the cup six hours after the absorption of the urine. The deodorizing effect was rated by causing 20 adult panel members to smell the interior of the cup at a position of about 3 cm from the upper part of the cup. For the sake of the rating, the panel members recorded the results of sensory test according to the following standard using a six-point scale and the recorded points were averaged. The test was performed by following the procedure while omitting the addition of water-absorbent resin (or water-absorbent resin composition) and using human urine alone. The product of this test was adopted as the standard. The deodorizing effect was rated by using the smell of this standard taken as the point 5 on the scale.

0: Absence of smell.
1: Barely discernible smell.
2: Discernible yet tolerable smell.
3: Easily discernible smell.
4: Strong smell.
5: Intense smell.

(e) Deodorizing Test (Rating of Absorbent Product)

Each of the absorbent products obtained in the examples and the comparative examples which will be described specifically herein below was cut to separate a circle (80 mm in diameter). On the bottom of a lidded propylene cup having an inner volume of 500 ml, the circle was placed with the liquid-permeable sheet held on the upper side. In the central part of the absorbent product, 20 g of human urine collected from 20 adults was placed. The cup was lidded and was wholly retained at 37° C. The lid was removed from the cup six hours thereafter. The deodorizing effect was rated by causing 20 adult panel members to smell the interior of the cup at a position of about 3 cm from the upper part of the cup. For the sake of the rating, the panel members recorded the results of sensory test according to the following standard using a six-point scale and the recorded points were averaged. The test was performed by following the procedure while omitting the addition of absorbent product and using human urine alone.

The product of this test was adopted as the standard. The deodorizing effect was rated by using the smell of this standard taken as the point 5 on the scale.

0: Absence of smell.
1: Barely discernible smell.
2: Discernible yet tolerable smell.
3: Easily discernible smell.
4: Strong smell.
5: Intense smell.

(f) Amount of the Hydrogen Sulfide Residue Under Wet (Test for Ability to Deodorize Hydrogen Sulfide)

In a glass petri dish (a product measuring 150 mm in outside diameter and 28 mm in height, entered under the code 305-08 in General Catalogue A-8000 published by Sogo Rikagaku Glass Seisakusho K.K. (in 2002)), a given water-absorbent resin (or water-absorbent resin composition) weighing 5.00 g was uniformly scattered. Then, one sheet of a gas-permeable and liquid-permeable Heatron paper (made by Nangoku Pulp Kogyo K.K. and sold under the product code of "GSP-22") cut into a circle was placed to cover the water-absorbent resin (or water-absorbent resin composition), with three portions of the circumference of the paper fixed to the inner wall of the glass petri dish with adhesive tape (10 mm×10 mm). Non-woven fabric was substituted for the paper when the Heatron paper was not available. A 3 L smelling bag (made by Ohmi Odo Air Service K.K.) was opened along one side to admit the glass petri dish having the water-absorbent resin (or water-absorbent resin composition) scattered thereon and then the opened part of the bag was closed so as to leave no gap behind. The smelling bag was provisionally decompressed via the glass tube part furnished for the smelling bag and then made to introduce a prescribed amount of odorless air. The amount of the odorless air to be introduced was so set that the total amount of the odorless air and the standard hydrogen sulfide gas to be introduced afterward would reach 2.5 L. The amount was set in accordance with the formula, amount of odorless air (L)=2.5−amount of standard hydrogen sulfide gas to be injected (L). Subsequently, 80 ml of an 0.90 mass % sodium chloride aqueous solution (physiological saline) adjusted to a temperature of 25±2° C. was poured without pausing into the petri dish inside the smelling bag by means of a glass funnel fitted with a polytetrafluoroethylene tube while preventing entry of ambient air so as to induce uniform swelling of the water-absorbent resin (or water-absorbent resin composition). The smelling bag was then tightly closed with a silicon rubber stopper. After the elapse of 30 minutes from the time of swelling, 1.0 ml of the standard hydrogen sulfide gas (hydrogen sulfide concentration: 5.06 (vol. %), the hydrogen sulfide concentration in the smelling bag: 20 ppm) was injected into the smelling bag with a syringe possessing an injection needle and was left standing therein at 25° C. The standard gas concentration and the amount of injection were properly varied so as to set the concentration in the bag at 20 ppm. After the elapse of 30 minutes, one hour, and three hours, the atmospheric concentration was determined by using a gas collecting device (made by Gastech K.K. and sold under the product code of "GV-100S") and a gas sensing tube (made by Gastech K.K. and sold under the product code of No 4LK") while preventing entry of ambient air. This atmospheric concentration was reported as the amount of the hydrogen sulfide residue under wet.

(g) Amount of Wet Ammonia Residue

In a glass petri dish (a product measuring 150 mm in outside diameter and 28 mm in height, entered under the code 305-08 in General Catalogue A-8000 published by Sogo Rikagaku Glass Seisakusho K.K. (in 2002), a given water-absorbent resin (or water-absorbent resin composition) weighing 5.00 g was uniformly scattered. Then, one sheet of a gas-permeable and liquid-permeable Heatron paper (made by Nangoku Pulp Kogyo K.K. and sold under the product code of "GSP-22") cut into a cycle was placed to cover the water-absorbent resin (or water-absorbent resin composition), with three portions of the circumference of the paper fixed to the inner wall of the glass petri dish with adhesive tape (10 mm×10 mm). Non-woven fabric was substituted for the paper when the Heatron paper was not available. A 3 L smelling bag (made by Ohmi Odo Air Service K.K.) was opened along one side to admit the glass petri dish having the water-absorbent resin (or water-absorbent resin composition) scattered thereon and then the opened part of the bag was closed so as to leave no gap behind. The smelling bag was provisionally decompressed via the glass tube part furnished for the smelling bag and then made to introduce a prescribed amount, i.e. 2.5 L, of odorless air. Subsequently, 80 ml of an 0.90 mass % sodium chloride aqueous solution (physiological saline) having the temperature adjusted to 25±2° C. and having 0.0132 mol of ammonia dissolved therein was poured without pausing into the petri dish inside the smelling bag by means of a glass funnel fitted with a polytetrafluoroethylene tube while preventing entry of ambient air so as to induce uniform swelling of the water-absorbent resin (or water-absorbent resin composition). The smelling bag was then tightly closed with a silicon rubber stopper and left standing at 25° C. After the elapse of 10 minutes, 30 minutes, and 60 minutes, the silicon rubber stopper was removed and the atmospheric concentration was determined by using a gas collecting device (made by Gastech K.K. and sold under the product code of "GV-100S") and a gas sensing tube (made by Gastech K.K. and sold under the product code of "No 3L, No. 3La, No. 3M") while preventing entry of ambient air. This atmospheric concentration was reported as the amount of wet ammonia residue.

(h) Separation Ratio (the Index Showing the Proportion of the Additives to the Water-Absorbent Resin Exfoliated from the Water-Absorbent Resin in a Swollen State)

An Erlenmeyer flask made of clear glass and having an inner volume of 200 ml (made by Sogo Rikagaku Glass Seisakusho K.K.) was packed with 0.50 parts by weight of a water-absorbent resin composition and 50 ml of 0.90 mass % sodium chloride aqueous solution (physiological saline) adjusted to a temperature of 25±2° C. Then, a stirrer (the standard type measuring 3 cmin length, made by Sogo Rikagaku Glass Seisakusho K.K.) was placed in the flask, and the flask was tightly closed with a silicon rubber stopper, and the content was stirred with a magnetic stirrer at 300 rpm for 10 minutes. After completion of the stirring, the flask was disposed in an ultrasonic cleaner (made by Shinnissei Denshi K.K., distributed by K.K. Baliba, and sold under the trademark designation of "Ultra-Sonic Cleaner 7500 Baliba"). Purified water was poured into the bath of the ultrasonic cleaner till it rose to the same height as the liquid level inside the flask. Then, the ultrasonic cleaner was operated for 20 minutes. Thereafter, the whole liquid in the flask was stirred again at 300 rpm for one minute so as to homogenize the liquid. Immediately after the elapse of this one minute, the content of the flask was subjected to filtration under reduced pressure (using a filter paper made by Advantec K.K. and sold under the product code of "No. 2"). The filtrate was wholly recovered and weighed to determine the mass W5 (g) thereof. The filtrate consequently obtained was tested for haze value by means of a digital haze meter (made by Nippon Denshoku Kogyo K.K. and sold under the trademark designation of "Automatic Digital Hazemeter NDH-20D"). The kaoline turbidity was calculated from the relation between the haze value and the kaoline turbidity. Further, from the calibration curve obtained by the method which will be specifically described herein below, the concentration X1 (ppm) of the additives in the filtrate, namely, the amount of the additives separated from the water-absorbent resin into the 0.90 mass % sodium chloride aqueous solution (physiological saline), was calculated.

The calibration curve described by the amounts of the individual additives and the kaoline turbidity was formed as follows. In an Erlenmeyer flask made of clear glass and having an inner volume of 200 ml (made by Sogo Rikagaku Glass Seisakusho K.K.), 50 ml of an 0.90 mass % sodium chloride aqueous solution (physiological saline) containing a prescribed amount (equivalent to 20 ppm, 50 ppm, 100 ppm, and 300 ppm) of additive and adjusted to a temperature of 25±2° C. was prepared. Then, a stirrer (the standard type measuring 3 cm in length, made by Sogo Rikagaku Glass Seisakusho K.K.) was placed in the flask, and the flask was tightly closed with a silicon rubber stopper, and the content was stirred with a magnetic stirrer at 300 rpm for 10 minutes. After completion of the stirring, an ultrasonic cleaner (made by Shinnissei Denshi K.K., distributed by K.K. Bariba, and sold under the trademark designation of "Ultra-Sonic Cleaner 7500 baliba") was disposed in the flask. Purified water was poured into the bath of the ultrasonic cleaner till it rose to the same height as the liquid level inside the flask. Then, the ultrasonic cleaner was operated for 20 minutes. Thereafter, the whole liquid in the flask was stirred again with a magnetic stirrer at 300 rpm for one minute so as to homogenize the liquid. Immediately after the elapse of one minute, the content of the flask was subjected to filtration under reduced pressure (using a filter paper made by Advantec K.K. and sold under the product code of "No. 2"). The filtrate was wholly recovered. The filtrate consequently obtained was tested for haze value by means of a digital haze meter (made by Nippon Denshoku Kogyo K.K. and sold under the trademark designation of "Automatic Digital Hazemeter NDH-20D"). The kaoline turbidity was calculated from the relation between the haze value and the kaoline turbidity. The relation between the known amount of additive and the kaoline turbidity was linearly approximated by the least-square method to form a calibration curve for each of the additives.

The separation ratio was calculated in accordance with the following formula.

Separation ratio (%)=X1/Y1×100

X1 (ppm): Concentration of additive in the filtrate calculated empirically

Y1 (ppm): Concentration of filtrate having the additive wholly separated from the water-absorbent resin and dispersed in the filtrate Y1 (ppm)=0.50×A1/100/W5×1000000

A1 (mass %): Amount of additive used (toward the water-absorbent resin)

W5 (g): Amount of filtrate

The formula indicates that the exfoliation of the additive from the water-absorbent resin decreases and the effect of the additive to be manifested gains in magnitude in accordance as the value of the separation ratio decreases.

(i) Hygroscopic Blocking Ratio (Mass %)

A given water-absorbent resin (or water-absorbent resin composition) weighing 2 g was uniformly scattered on the bottom of an aluminum cup measuring 52 mm in diameter of the bottom surface and 22 mm in height. The cup containing the water-absorbent resin was quickly placed in a thermo-humidistat (made by Tabai Espec k.k. and sold under the trademark designation of "Platioodus Lucifer PL-2G") adjusted in advance to 25° C. and RH 90% and left standing therein for 60 minutes. Then, the water-absorbent resin (or water-absorbent resin composition) which had absorbed moisture was transferred onto a JIS standard sieve measuring 7.5 cm in diameter and having an aperture of 2000 μm. When the moistened water-absorbent resin (or water-absorbent resin composition) happened to adhere strongly to the aluminum cup and defy transfer to the sieve, the water-absorbent resin (or water-absorbent resin composition) which had absorbed moisture and had undergone the phenomenon of blocking was peeled off heedfully to avoid inflicting breakage and then transferred to the sieve. The water-absorbent resin in the sieve was immediately shaken for 8 seconds with a shaking classifier (Iida sieve shaker, Type ES-65, SER No. 0501) to determine the amount, W6 (g), of the water-absorbent resin (or water-absorbent resin composition) stopped on the sieve and the amount, W7 (g), of the water-absorbent resin (or water-absorbent resin composition) passed through the sieve.

The hygroscopic blocking ratio (mass %) was calculated in accordance with the following formula. The formula indicates that the hygroscopic fluidity gained in excellence and the powder handling property gained in enhancement in accordance as the hygroscopic blocking ratio decreased. Hygroscopic blocking ratio (mass %)=Weight, w6 (g)/(weight W6 (g)+weight W7 (g))×100

(j) Gel Strength

Each water-absorbent resin composition 2 g were swelled with synthetic urine containing 0.005 mass % L-ascorbic acid (composed of 95 g of urea, 40 g of sodium chloride, 5 g of magnesium sulfate, 5 g of calcium chloride and 4855 g of deionized water) to 25 times the original volume thereof and then left standing for prescribed period at 37□C and RH 90%. After the elapse of the 24 hours, anti-degradation ability toward urine was measured by the time (second) necessary for 2 cm movement of the edge of the fluidized gel when vessel was inclined at 90 degree. Further, resultant swelled gel was checked with tactile impression in accordance with the following standard (◯: good, Δ: so so, X: bad). Incidentally, the smaller value (second) means higher anti-degradation ability toward urine and durability.

Referential Example 1

A reaction solution was obtained by dissolving 3.4 g of polyethylene glycol diacrylate (the average addition mol number of ethylene oxide 8) in 5500 g of sodium acrylate aqueous solution (monomer concentration 38 mass %) having a neutralizing ratio of 75 mol %. Then, this reaction solution was deaerated under an atmosphere of nitrogen gas for 30 minutes. The reaction solution mentioned above was subsequently supplied to a reaction vessel formed by attaching a lid to a twin arm type jacketed kneader made of stainless steel, furnished with two sigma type vanes, and having an inner volume of 10 L. The system having the reaction solution kept at 30° C. was displaced with nitrogen gas. When 2.46 g of sodium persulfate and 0.10 g of L-ascorbic acid were added to the reaction solution while the reaction solution was continuously kept stirred, polymerization was started about one minute thereafter. Then, the polymerization was carried out at 30° C.-90° C. A polymer of the hydrogel form was extracted from the reaction vessel 60 minutes after the start of the polymerization. The hydrogel polymer thus obtained was finely divided into particles 1-4 mm in diameters. The finely divided hydrogel polymer was spread on a 50-mesh metal sheet (having a mesh size of 300 μm) and dried with hot air at 150° C. for 90 minutes. Then, the dried particles were pulverized by the use of a shaking mill, further classified with a metal sheet having an aperture of 20 mesh (having a mesh size of 850 μm). And, the classified particles were blended to obtain an amorphously pulverized water-absorbent resin powder (a).

100 parts by weight of the water-absorbent resin powder (a) was mixed with 3.83 parts by weight of a surface cross-linking agent composed of 0.5 parts by weight of propylene glycol, 0.03 parts by weight of ethylene glycol diglycidyl ether, 0.3 parts by weight of 1,4-butane diol, and 3 parts by weight of water. A water-absorbent resin (1) was obtained by subjecting the resultant mixture to a heat treatment at 210° C. for 55 minutes. The absorption capacity without load, the absorption capacity under the pressure, and the particle size distribution of this water-absorbent resin (1) are shown in Table 1.

Referential Example 2

A reaction solution was formed by dissolving 5.9 g of polyethylene glycol diacrylate (average addition mol number of ethylene oxide 8) in 5500 g of sodium acrylate aqueous solution (monomer concentration 38 mass %) having a neutralizing ratio of 65 mol %. Then, this reaction solution was deaerated in the same manner as in Referential Example 1 and supplied to the same reaction vessel as in Referential Example 1. The system having the reaction solution kept at 30° C. was displaced with nitrogen gas. Subsequently, when the reaction solution was continuously stirred and 2.46 g of sodium persulfate and 0.10 g of L-ascorbic acid were added to the stirred reaction solution, polymerization was started about one minute thereafter. The polymerization was carried out at 30° C.-90° C. A polymer of the hydrogel form was extracted from the reaction vessel 60 minutes thereafter. The hydrogel polymer thus obtained was finely divided into particles about 1-4 mm in diameters. This hydrogel polymer was dried and pulverized in the same manner as in Referential Example 1 and further classified with a metal sheet having an aperture of 20 mesh (mesh size 850 μm). And, the classified particles were blended to obtain an amorphously pulverized water-absorbent resin powder (b).

100 parts by weight of the water-absorbent resin powder (b) thus obtained was mixed with 3.8 parts by weight of a surface cross-linking agent composed of 0.5 parts by weight of propylene glycol, 0.3 parts by weight of 1,4-butane diol, and 3 parts by weight of water. A water-absorbent resin (2) was obtained by subjecting the resultant mixture to a heat treatment at 200° C. for 45 minutes. The results are shown in Table 1.

Referential Example 3

A reaction solution was formed by dissolving 3.6 g of polyethylene glycol diacrylate (average addition mol number of ethylene oxide 8) in 5500 g of sodium acrylate aqueous solution (monomer concentration 33 mass %) having a neutralizing ratio of 60 mol %. Then, this reaction solution was deaerated in the same manner as in Referential Example 1 and supplied to the same reaction vessel as in Referential Example 1. The system having the reaction solution kept at 30° C. was displaced with nitrogen gas. Subsequently, when the reaction solution was continuously stirred and 2.46 g of sodium persulfate and 0.10 g of L-ascorbic acid were added to the stirred reaction solution, polymerization was started about one minute thereafter. The polymerization was carried out at 30° C.-85° C. A polymer of the hydrogel form was extracted from the reaction vessel 60 minutes thereafter. The hydrogel polymer thus obtained was finely divided into particles about 1-4 mm in diameters. This hydrogel polymer was dried and pulverized in the same manner as in Referential Example 1 and further classified with a metal sheet having an aperture of 20 mesh (mesh size 850 μm). And, the classified particles were blended to obtain an amorphously pulverized water-absorbent resin powder (c).

100 parts by weight of the water-absorbent resin powder (c) thus obtained was mixed with 3.83 parts by weight of a surface cross-linking agent having the same composition as in Referential Example 1. A water-absorbent resin (3) was obtained by subjecting the resultant mixture to a heat treatment at 195° C. for 40 minutes. The results are shown in Table 1.

Referential Example 4

A reaction solution was formed by dissolving 3.3 g of polyethylene glycol diacrylate (average addition mol number of ethylene oxide 8) in 5500 g of sodium acrylate aqueous solution (monomer concentration 30 mass %) having a neutralizing ratio of 55 mol %. Then, this reaction solution was deaerated in the same manner as in Referential Example 1 and supplied to the same reaction vessel as in Referential Example 1. The system having the reaction solution kept at 30° C. was displaced with nitrogen gas. Subsequently, when the reaction solution was continuously stirred and 2.46 g of sodium persulfate and 0.10 g of L-ascorbic acid were added to the stirred reaction solution, polymerization was started about one minute thereafter. The polymerization was carried out at 30° C.-85° C. A polymer of the hydrogel form was extracted from the reaction vessel 60 minutes thereafter. The hydrogel polymer thus obtained was finely divided into particles about 1-4 mm in diameters. This hydrogel polymer was dried and pulverized in the same manner as in Referential Example 1 and further classified with a metal sheet having an aperture of 20 mesh (mesh size 850 μm). And, the classified particles were blended to obtain an amorphously pulverized water-absorbent resin powder (d).

100 parts by weight of the water-absorbent resin powder (d) thus obtained was mixed with 3.8 parts by weight of a surface cross-linking agent of the same composition as in Referential Example 2. A water-absorbent resin (4) was obtained by subjecting the resultant mixture to a heat treatment at 195° C. for 40 minutes. The results are shown in Table 1.

Referential Example 5

A reaction solution was formed by dissolving 5.3 g of polyethylene glycol diacrylate (average addition mol number of ethylene oxide 8) in 6600 g of sodium acrylate aqueous solution (monomer concentration 35.5 mass %) having a neutralizing ratio of 68 mol %. Then, this reaction solution was deaerated in the same manner as in Referential Example 1 and supplied to the same reaction vessel as in Referential Example 1. The system having the reaction solution kept at 30° C. was displaced with nitrogen gas. Subsequently, when the reaction solution was continuously stirred and 3.23 g of sodium persulfate and 0.016 g of L-ascorbic acid were added to the reaction solution, polymerization was started about one minute thereafter. The polymerization was carried out at 30° C.-90° C. A polymer of the hydrogel form was extracted from the reaction vessel 40 minutes thereafter. The hydrogel polymer thus obtained was finely divided into particles about 1-4 mm in diameters. The hydrogel polymer was spread on a metal sheet having an aperture of 50 mesh (mesh size 300 μm) and dried with hot air at 170° C. for 40 minutes. Then, the dried particles were pulverized by the use of a shaking mill, further classified with a metal sheet having an aperture of 20 mesh (having a mesh size of 850 μm). And, the classified particles were blended to obtain an amorphously pulverized water-absorbent resin powder (e).

100 parts by weight of the water-absorbent resin powder (e) thus obtained was mixed with 3.55 parts by weight of a surface cross-linking agent composed of 0.51 parts by weight of propylene glycol, 0.31 parts by weight of 1,4-butane diol, and 2.73 parts by weight of water. A water-absorbent resin (5) was obtained by subjecting the resultant mixture to a heat treatment at 200° C. for 40 minutes. The results are shown in Table 1.

Referential Example 6

A reaction solution was formed by dissolving 5.6 g of polyethylene glycol diacrylate. (average addition mol number of ethylene oxide 8) in 6600 g of sodium acrylate aqueous solution (monomer concentration 38 mass %) having a neutralizing ratio of 72 mol %. Then, this reaction solution was deaerated in the same manner as in Referential Example 1 and supplied to the same reaction vessel as in Referential Example 1. The system having the reaction solution kept at 30° C. was displaced with nitrogen gas. Subsequently, when the reaction solution was continuously stirred and 3.42 g of sodium persulfate and 0.017 g of L-ascorbic acid were added to the stirred reaction solution, polymerization was started about one minute thereafter. The polymerization was carried out at 30° C.-90° C. A polymer of the hydrogel form was extracted from the reaction vessel 40 minutes thereafter. The hydrogel polymer thus obtained was finely divided into particles about 1-4 mm in diameters. This hydrogel polymer was spread on a 50-mesh metal sheet (having a mesh size of 300 μm). Then, the hydrogel polymer was dried and pulverized in the same manner as in the Referential Example 1, and classified with a metal sheet having an aperture of 20 mesh (having a mesh size of 850 μm). And, the classified particles were blended to obtain an amorphously pulverized water-absorbent resin powder (f).

100 parts by weight of the water-absorbent resin powder (f) thus obtained was mixed with 3.55 parts by weight of a surface cross-linking agent having the same composition as in Referential Example 5. A water-absorbent resin (6) was obtained by subjecting the resultant mixture to a heat treatment at 200° C. for 50 minutes. The results are shown in Table 1.

Referential Example 7

A reaction solution was formed by dissolving 3.1 g of polyethylene glycol diacrylate. (average addition mol number of ethylene oxide 8) in 5500 g of sodium acrylate aqueous solution (monomer concentration 33 mass %) having a neutralizing ratio of 65 mol %. Then, this reaction solution was deaerated in the same manner as in Referential Example 1 and supplied to the same reaction vessel as in Referential Example 1. The system having the reaction solution kept at 30° C. was displaced with nitrogen gas. Subsequently, when the reaction solution was continuously stirred and 2.46 g of sodium persulfate and 0.10 g of L-ascorbic acid were added to the stirred reaction solution, polymerization was started about one minute thereafter. The polymerization was carried out at 30° C.-85° C. A polymer of the hydrogel form was extracted from the reaction vessel 60 minutes thereafter. The hydrogel polymer thus obtained was finely divided into particles about 1-4 mm in diameters. This hydrogel polymer was spread on a 50-mesh metal sheet (having a mesh size of 300 μm). Then, the hydrogel polymer was dried and pulverized in the same manner as in the Referential Example 1, and classified with a metal sheet having an aperture of 20 mesh (having a mesh size of 850 μm). And, the classified particles were blended to obtain an amorphously pulverized water-absorbent resin powder (g).

100 parts by weight of the water-absorbent resin powder (g) thus obtained was mixed with 3.83 parts by weight of a surface cross-linking agent having the same composition as in Referential Example 1. A water-absorbent resin (7) was obtained by subjecting the resultant mixture to a heat treatment at 195° C. for 60 minutes. The results are shown in Table 1.

Referential Example 8

A reaction solution was formed by dissolving 6.8 g of polyethylene glycol diacrylate. (average addition mol number of ethylene oxide 8) in 5500 g of sodium acrylate aqueous solution (monomer concentration 20 mass %) having a neutralizing ratio of 30 mol %. Then, this reaction solution was deaerated in the same manner as in Referential Example 1 and supplied to the same reaction vessel as in Referential Example 1. The system having the reaction solution kept at 30° C. was displaced with nitrogen gas. Subsequently, when the reaction solution was continuously stirred and 2.46 g of sodium persulfate and 0.10 g of L-ascorbic acid were added to the stirred reaction solution, polymerization was started about one minute thereafter. The polymerization was carried out at 30° C.-80° C. A polymer of the hydrogel form was extracted from the reaction vessel 60 minutes thereafter. The hydrogel polymer thus obtained was finely divided into particles about 1-4 mm in diameters. This finely divided hydrogel polymer was spread on a 50-mesh metal sheet (having a mesh size of 300 μm). Then, the hydrogel polymer was dried and pulverized in the same manner as in the Referential Example 1, and classified with a metal sheet having an aperture of 20 mesh (having a mesh size of 850 μm). And, the classified particles were blended to obtain an amorphously pulverized water-absorbent resin powder (h).

100 parts by weight of the water-absorbent resin powder (h) thus obtained was mixed with 3.8 parts by weight of a surface cross-linking agent having the same composition as in Referential Example 2. A water-absorbent resin (8) was obtained by subjecting the resultant mixture to a heat treatment at 210° C. for 50 minutes. The results are shown in Table 1.

Referential Example 9

An amorphously pulverized water-absorbent resin powder (i) was obtained by following the procedure of Referential Example 1. The water-absorbent resin powder (i) thus obtained was labeled in its unmodified form as "absorbent resin (9)." The results are shown in Table 1.

Referential Example 10

In a beaker having an inner volume of 5 L, 1 L of purified water was placed and then stirred and retained by heating at a temperature of 60° C. Then, 2 L of an aqueous solution having 114.5 parts by weight of zinc sulfate (made by Wako Pure Chemical Industries, Ltd.) and 17.6 parts by weight of sodium silicate powder (made by Wako Pure Chemical Industries, Ltd.) mixed therein and an ammonia aqueous solution were added dropwise to the purified water heedfully so as to retain the pH value at 7.5. A complex oxide hydrate containing zinc and silicate (B1) was obtained by separating the resultant precipitate by filtration, washing the separated precipitate, and drying the washed precipitate at 120° C. for six hours.

Referential Example 11

In a beaker having an inner volume of 5 L, 1 L of purified water was placed and then stirred and retained by heating at a temperature of 60° C. Then, 2 L of an aqueous solution having 132.9 parts by weight of zinc sulfate (made by Wako Pure Chemical Industries, Ltd.) and 110.1 parts by weight of aluminum sulfate 14-18 hydrate (made by Wako Pure Chemical Industries, Ltd.) mixed therein and an aqueous ammonia solution were added dropwise to the purified water heedfully so as to retain the pH value at 7.5. A complex oxide hydrate containing zinc and aluminum (B2) (mass ratio of zinc and aluminum 85/15) was obtained by separating the resultant precipitate by filtration, washing the separated precipitate, and drying the washed precipitate at 120° C. for six hours.

Referential Example 12

In a beaker having an inner volume of 5 L, 1 L of purified water was placed and then stirred and retained by heating at a temperature of 60° C. Then, 2 L of an aqueous solution having 161.2 parts by weight of titanium chloride (made by Wako Pure Chemical Industries, Ltd.) and 9.1 parts by weight of sodium silicate powder (made by Wako Pure Chemical Industries, Ltd.) mixed therein and an ammonia aqueous solution were added dropwise to the purified water heedfully so as to retain the pH value at 7.5. A complex oxide hydrate containing titanium and silicon (B3) (mass ratio of titanium and silicon: 91/9) was obtained by separating the resultant precipitate by filtration, washing the separated precipitate, and drying the washed precipitate at 120° C. for six hours.

Referential Example 13

A reaction solution was formed by dissolving 2.3 g of polyethylene glycol diacrylate (average addition mol number of ethylene oxide 8) in 5500 g of sodium acrylate aqueous solution (monomer concentration 38 mass %) having a neutralizing ratio of 75 mol %. Then, this reaction solution was deaerated in the same manner as in Referential Example 1 and supplied to the same reaction vessel as in Referential Example 1. The system having the reaction solution kept at 30° C. was displaced with nitrogen gas. Subsequently, when the reaction solution was continuously stirred and 2.83 g of sodium persulfate and 0.024 g of L-ascorbic acid were added to the stirred reaction solution, polymerization was started about one minute thereafter. The polymerization was carried out at 30° C.-100° C. A polymer of the hydrogel form was extracted from the reaction vessel 60 minutes thereafter. The hydrogel polymer thus obtained was finely divided into particles about 1-4 mm in diameters. An amorphously pulverized water-absorbent resin powder (j) was obtained by spreading the finely divided hydrogel polymer on a metal sheet having an aperture of 50 mesh (mesh size 300 μm) and further classifying and proportionating it with a metal sheet having an aperture of 20 mesh (mesh size 850 μm).

100 parts by weight of the water-absorbent resin powder (j) thus obtained was mixed with 3.83 parts by weight of a surface cross-linking agent having the same composition as in Referential Example 1. A water-absorbent resin (10) was obtained by subjecting the resultant mixture to a heat treatment at 195° C. for 30 minutes. The results are shown in Table 1.

Example 1

A water-absorbent resin composition (1) was obtained by adding 100 parts by weight of the water-absorbent resin (1) obtained in Referential Example 1 and 0.50 mass part of a complex oxide hydrate of zinc and silicon (mass ratio of contents of zinc and silicon: 82/18 and average particle diameter: 0.36 μm; made by Titan Kogyo K.K. and sold under the trademark designation of "Ceratiox SZ-100S") together and mixing them (dry blend).

The water-absorbent resin composition (1) consequently obtained was tested for absorption capacity without load, absorption capacity under the pressure of 1.9 kPa, ability to deodorize hydrogen sulfide, ability to deodorize ammonia, performance of deodorization, separation ratio, and hygroscopic blocking ratio. The results are shown in Table 2, Table 3, and Table 4.

Example 2

A water-absorbent resin composition (2) was obtained by following the procedure of Example 1 while changing the water-absorbent resin (1) obtained in Referential Example 1 to the water-absorbent resin. (2) obtained in Referential Example 2. The water-absorbent resin composition (2) was tested in the same manner as in Example 1. The results are shown in Table 2 and Table 3.

Example 3

A water-absorbent resin composition (3) was obtained by following the procedure of Example 1 while changing the water-absorbent resin (1) obtained in Referential Example 1 to the water-absorbent resin (3) obtained in Referential Example 3. The water-absorbent resin composition (3) was tested in the same manner as in Example 1. The results are shown in Table 2 and Table 3.

Example 4

A water-absorbent resin composition (4) was obtained by following the procedure of Example 1 while changing the water-absorbent resin (1) obtained in Referential Example 1 to the water-absorbent resin (4) obtained in Referential Example 4. The water-absorbent resin composition (4) was tested in the same manner as in Example 1. The results are shown in Table 2 and Table 3.

Example 5

A water-absorbent resin composition (5) was obtained by following the procedure of Example 1 while changing the water-absorbent resin (1) obtained in Referential Example 1 to the water-absorbent resin (5) obtained in Referential Example 5. The water-absorbent resin composition (5) was tested in the same manner as in Example 1. The results are shown in Table 2 and Table 3.

Example 6

A water-absorbent resin composition (6) was obtained by following the procedure of Example 1 while changing the water-absorbent resin (1) obtained in Referential Example 1 to the water-absorbent resin. (6) obtained in Referential Example 6. The water-absorbent resin composition (6) was tested in the same manner as in Example 1. The results are shown in Table 2 and Table 3.

Example 7

A water-absorbent resin composition (7) was obtained by following the procedure of Example 1 while changing the water-absorbent resin (1) obtained in Referential Example 1 to the water-absorbent resin (5) obtained in Referential Example 5 and additionally using 0.5 parts by weight of 15 mass % aqueous solution of the extract from leaves of a theaceous plants (sold by Shiraimatsu Shinyaku K.K. [located at 37-1 Ugawa, Mizuguchi-town, Koga-country, Shiga-prefecture]under the product code of "FS-80MO") as a plant component. The water-absorbent resin composition (7) was tested in the same manner as in Example 1. The results are shown in Table 2 and Table 3.

Example 8

A water-absorbent resin composition (8) was obtained by following the procedure of Example 1 while changing the complex oxide hydrate of zinc and silicon to the complex oxide hydrate of zinc and silicon (B1) (mass ratio of zinc and silicon: 90/10) obtained in Referential Example 10. The water-absorbent resin composition (8) was tested in the same manner as in Example 1. The results are shown in Table 2, Table 3, and Table 4.

Example 9

A water-absorbent resin composition (9) was obtained by following the procedure of Example 1 while changing the complex oxide hydrate of zinc and silicon to the complex oxide hydrate of zinc and aluminum (B2) obtained in Referential Example 11. The water-absorbent resin composition (9) was tested in the same manner as in Example 1. The results are shown in Table 2, Table 3, and Table 4.

Example 10

A water-absorbent resin composition (10) was obtained by following the procedure of Example 1 while changing the amount of the complex oxide hydrate of zinc and silicon to 0.10 parts by weight. The water-absorbent resin composition (10) was tested in the same manner as in Example 1. The results are shown in Table 2, Table 3, and Table 4.

Example 11

A water-absorbent resin composition (11) was obtained by following the procedure of Example 1 while changing the water-absorbent resin (1) obtained in Referential Example 1 to the water-absorbent resin (10) obtained in Referential Example 13. The water-absorbent resin composition (11) was tested in the same manner as in Example 1. The results are shown in Table 2 and Table 3.

Comparative Example 1

A comparative water-absorbent resin composition (1) was obtained by following the procedure of Example 1 while changing the water-absorbent resin (1) obtained in Referential Example 1 to the water-absorbent resin (7) obtained in Referential Example 7. The comparative water-absorbent resin composition (1) was tested in the same manner as in Example 1. The results are shown in Table 2 and Table 3.

Comparative Example 2

A comparative water-absorbent resin composition (2) was obtained by following the procedure of Example 1 while changing the water-absorbent resin (1) obtained in Referential Example 1 to the water-absorbent resin (8) obtained in Referential Example 8. The comparative water-absorbent resin composition (2) was tested in the same manner as in Example 1. The results are shown in Table 2 and Table 3.

Comparative Example 3

A comparative water-absorbent resin composition (3) was obtained by following the procedure of Example 1 while changing the water-absorbent resin (1) obtained in Referential Example 1 to the water-absorbent resin (9) obtained in Referential Example 9. The comparative water-absorbent resin composition (3) was tested in the same manner as in Example 1. The results are shown in Table 2 and Table 3.

Comparative Example 4

A comparative water-absorbent resin composition (4) was obtained by following the procedure of Example 1 while omitting the addition of the complex oxide hydrate of zinc and silicon. The comparative water-absorbent resin composition (4) was tested in the same manner as in Example 1. The results are shown in Table 2, Table 3, and Table 4.

Comparative Example 5

A comparative water-absorbent resin composition (5) was obtained by following the procedure of Example 1 while changing the complex oxide hydrate of zinc and silicon to a complex oxide hydrate having a different mass ratio of contents of zinc and silicon and a different particle diameter (mass ratio of contents of zinc and silicon: 40/60, particle diameter: not more than 250 µm: made by Rasa Kogyo K.K. and sold under the trademark designation of "Shukurenzu KD-211S"). The comparative water-absorbent resin composition (5) was tested in the same manner as in Example 1. The results are shown in Table 2, Table 3, and Table 4.

Comparative Example 6

A comparative water-absorbent resin composition (6) was obtained by following the procedure of Example 1 while changing the complex oxide hydrate of zinc and silicon to a complex oxide hydrate having a different mass ratio of contents of zinc and silicon and a different particle diameter (mass ratio of contents of zinc and silicon: 40/60, particle diameter: not more than 1 µm: made by Rasa Kogyo K.K. and sold under the trademark designation of "Shukurenzu KD-211G"). The comparative water-absorbent resin composition (6) was tested in the same manner as in Example 1. The results are shown in Table 2, Table 3, and Table 4.

Comparative Example 7

A comparative water-absorbent resin composition (7) was obtained by following the procedure of Example 1 while changing the complex oxide hydrate of zinc and silicon to a complex oxide hydrate having a different combination of metal elements, i.e. titanium and zinc (mass ratio of contents of titanium and zinc: 50/50, average particle diameter: 0.50 µm: made by Titan Kogyo K.K. and sold under the trademark designation of "Ceratiox TZ-100"). The comparative water-absorbent resin composition (7) was tested in the same manner as in Example 1. The results are shown in Table 2, Table 3, and Table 4.

Comparative Example 8

A comparative water-absorbent resin composition (8) was obtained by following the procedure of Example 1 while changing the complex oxide hydrate of zinc and silicon to a basic zinc carbonate as a zinc compound (made by Wako Pure Chemical Industries, Ltd.). The comparative water-absorbent resin composition (8) was tested in the same manner as in Example 1. The results are shown in Table 2, Table 3, and Table 4.

Comparative Example 9

A comparative water-absorbent resin composition (9) was obtained by following the procedure of Example 1 while changing the complex oxide hydrate of zinc and silicon to zinc oxide, which is oxide of only zinc, (average particle diameter: 31 nm: made by CI Kasei K.K. and sold under the trademark designation of "Nanotec ZnO"). The comparative water-absorbent resin composition (9) was tested in the same manner as in Example 1. The results are shown in Table 2, Table 3, and Table 4.

Comparative Example 10

A comparative water-absorbent resin composition (10) was obtained by following the procedure of Example 1 while changing the complex oxide hydrate of zinc and silicon to silicon dioxide, which is oxide of only silicon, (average particle diameter: 26 nm: made by CI Kasei K.K. and sold under the trademark designation of "Nanotec $SiO_2$"). The comparative water-absorbent resin composition (10) was tested in the same manner as in Example 1. The results are shown in Table 2, Table 3, and Table 4.

Comparative Example 11

A comparative water-absorbent resin composition (11) was obtained by following the procedure of Example 1 while changing the complex oxide hydrate of zinc and silicon to titanium dioxide, which is oxide of only titanium, (average particle diameter: 30 nm: made by CI Kasei K.K. and sold under the trademark designation of "Nanotec $TiO_2$"). The comparative water-absorbent resin composition (11) was tested in the same manner as in Example 1. The results are shown in Table 2, Table 3, and Table 4.

Comparative Example 12

A comparative water-absorbent resin composition (12) was obtained by following the procedure of Example 1 while changing the complex oxide hydrate of zinc and silicon to the complex oxide hydrate (B3) of titanium and silicon obtained in Referential Example 12. The comparative water-absorbent resin composition (12) was tested in the same manner as in Example 1. The results are shown in Table 2, Table 3, and Table 4.

Comparative Example 13

A comparative water-absorbent resin composition (12) was obtained by following the procedure of Example 1 while changing the complex oxide hydrate of zinc and silicon to the mixture of the zinc oxide and the silicon dioxide (obtained by mixing the zinc oxide and the silicon dioxide at a ratio of 1/1). The comparative water-absorbent resin composition (12) was tested for absorption capacity without load, absorption capacity under the pressure of 1.9 kPa, performance of deodorization of hydrogen sulfide, property of deodorizing ammonia, and deodorization. The results are shown in Table 2 and Table 3.

Example 11

In a mixer, 37 parts by weight of the water-absorbent resin composition (1) obtained in Example 1 and 63 parts by weight of ground wood pulp were dry mixed. Then, the resultant mixture was pneumatically spread on a wire screen formed in an aperture of 400 mesh (mesh size 38 μm) by the use of a batch type pneumatic sheet producing device. Consequently, a web measuring 130 mm×400 mm was obtained. When this web was pressed under the pressure of 196.14 kPa for five seconds, it produced an absorbent material having a basis weight of about 0.05 g/cm².

Then, a pad type adult disposable diaper as an absorbent product was obtained by pasting a liquid-impermeable backsheet made of liquid-impermeable polypropylene, the absorbent material mentioned above, and a topsheet of non-woven fabric made of a liquid-permeable polypropylene sequentially in the order mentioned. This absorbent product (1) had a mass of 50 g.

The absorbent product (1) was tested for deodorizing property. The results are shown collectively in Table 5.

Examples 12-14

Absorbent products (2), (3), and (4) were obtained by following the procedure of Example 11 while changing the water-absorbent resin composition (1) respectively to the water-absorbent resin compositions (8), (9), and (10).

The absorbent products (2), (3), and (4) thus obtained were tested for deodorizing property. The results are shown collectively in Table 5.

Comparative Examples 14-17

The comparative absorbent products (1), (2), (3), and (4) were obtained by following the procedure of Example 10 while changing the water-absorbent resin composition (1) respectively to the comparative water-absorbent resin compositions (4), (5), (7), and (13) obtained in Comparative Examples 4, 5, 7, and 13.

The comparative absorbent products (1), (2), (3), and (4) thus obtained were tested for deodorizing property. The results are shown collectively in Table 5.

Example 15

Water-absorbent resin composition (1), (8), and (9) and comparative water-absorbent resin composition (4) were tested for anti-degradation ability toward urine in accordance with the procedure (j). The result is as follows. Example 1: ○ (more than 60 seconds), Example 8: ○ (more than 60 seconds), Example 9: ○ (more than 60 seconds), Comparative Example 4: ×(10 seconds).

TABLE 1

| | Water-absorbent resin | Absorption capacity without load (g/g) | Absorption capacity under the pressure of 1.9 KPa (g/g) | Particle diameter distribution (mass %) | | | | |
|---|---|---|---|---|---|---|---|---|
| | | | | 850 μm≤ | 650 μm≤ <850 μm | 300 μm≤ <600 μm | 150 μm≤ <300 μm | <150 μm |
| Referential Example 1 | Water-absorbent resin (1) | 35 | 32 | 0 | 16 | 58 | 22 | 4 |
| Referential Example 2 | Water-absorbent resin (2) | 31 | 30 | 0 | 14 | 70 | 15 | 2 |
| Referential Example 3 | Water-absorbent resin (3) | 35 | 32 | 0 | 17 | 65 | 16 | 2 |

TABLE 1-continued

| | Water-absorbent resin | Absorption capacity without load (g/g) | Absorption capacity under the pressure of 1.9 KPa (g/g) | Particle diameter distribution (mass %) | | | | |
|---|---|---|---|---|---|---|---|---|
| | | | | 850 μm≤ | 650 μm≤ <850 μm | 300 μm≤ <600 μm | 150 μm≤ <300 μm | <150 μm |
| Referential Example 4 | Water-absorbent resin (4) | 34 | 31 | 0 | 20 | 65 | 14 | 1 |
| Referential Example 5 | Water-absorbent resin (5) | 33 | 30 | 0 | 23 | 60 | 15 | 2 |
| Referential Example 6 | Water-absorbent resin (6) | 26 | 27 | 0 | 23 | 58 | 17 | 2 |
| Referential Example 7 | Water-absorbent resin (7) | 42 | 12 | 0 | 3 | 52 | 37 | 8 |
| Referential Example 8 | Water-absorbent resin (8) | 22 | 18 | 0 | 13 | 69 | 16 | 2 |
| Referential Example 9 | Water-absorbent resin (9) | 45 | 13 | 0 | 16 | 58 | 22 | 4 |
| Referential Example 13 | Water-absorbent resin (10) | 48 | 23 | 0 | 0 | 44 | 47 | 9 |

TABLE 2

| | Water-absorbent resin composition | Absorption capacity without load (g/g) | Absorption capacity under the pressure of 1.9 KPa (g/g) | Amount of the hydrogen sulfide residue under wet (ppm) | | | Amount of wet ammonia residue (ppm) | | |
|---|---|---|---|---|---|---|---|---|---|
| | | | | 30 min | 60 min | 180 min | 10 min | 30 min | 60 min |
| Example 1 | Water-absorbent resin composition (1) | 36 | 32 | 2.0 | 1.0 | 0.0 | 220 | 90 | 60 |
| Example 2 | Water-absorbent resin composition (2) | 31 | 30 | 2.5 | 1.5 | 1.0 | 120 | 40 | 10 |
| Example 3 | Water-absorbent resin composition (3) | 35 | 32 | 2.5 | 1.5 | 1.0 | 100 | 20 | 5 |
| Example 4 | Water-absorbent resin composition (4) | 34 | 31 | 3.0 | 2.0 | 1.5 | 90 | 30 | 5 |
| Example 5 | Water-absorbent resin composition (5) | 33 | 30 | 3.0 | 1.5 | 0.0 | 120 | 40 | 15 |
| Example 6 | Water-absorbent resin composition (6) | 26 | 27 | 2.5 | 1.0 | 0.0 | 180 | 70 | 50 |
| Example 7 | Water-absorbent resin composition (7) | 33 | 30 | 2.0 | 1.5 | 0.0 | 120 | 40 | 15 |
| Example 8 | Water-absorbent resin composition (8) | 34 | 28 | 2.0 | 1.0 | 0.0 | 200 | 80 | 60 |
| Example 9 | Water-absorbent resin composition (9) | 34 | 28 | 2.5 | 1.5 | 0.5 | 210 | 80 | 60 |
| Example 10 | Water-absorbent resin composition (10) | 36 | 31 | 6.0 | 5.0 | 5.0 | 250 | 80 | 70 |
| Example 11 | Water-absorbent resin composition (11) | 48 | 21 | 5.0 | 3.0 | 1.5 | 200 | 80 | 50 |
| Comparative Example 1 | Comparative water-absorbent resin composition (1) | 42 | 12 | 11.0 | 8.0 | 6.0 | 230 | 150 | 100 |
| Comparative Example 2 | Comparative water-absorbent resin composition (2) | 22 | 18 | 10.0 | 8.0 | 7.0 | 200 | 130 | 60 |
| Comparative Example 3 | Comparative water-absorbent resin composition (3) | 45 | 13 | 11.0 | 9.0 | 7.0 | 250 | 120 | 60 |
| Comparative Example 4 | Comparative water-absorbent resin composition (4) | 35 | 31 | 15.0 | 14.5 | 14.0 | 430 | 110 | 50 |
| Comparative Example 5 | Comparative water-absorbent resin composition (5) | 35 | 30 | 10.5 | 7.0 | 3.0 | 300 | 110 | 70 |
| Comparative Example 6 | Comparative water-absorbent resin composition (6) | 35 | 29 | 8.0 | 4.5 | 1.5 | 280 | 120 | 75 |
| Comparative Example 7 | Comparative water-absorbent resin composition (7) | 34 | 28 | 7.5 | 6.5 | 5.0 | 300 | 130 | 100 |
| Comparative Example 8 | Comparative water-absorbent resin composition (8) | 34 | 27 | 12.0 | 10.5 | 9.5 | 400 | 150 | 80 |
| Comparative Example 9 | Comparative water-absorbent resin composition (9) | 35 | 30 | 11.0 | 9.5 | 8.0 | 410 | 140 | 90 |
| Comparative Example 10 | Comparative water-absorbent resin composition (10) | 35 | 25 | 14.5 | 14.5 | 13.5 | 230 | 90 | 60 |
| Comparative Example 11 | Comparative water-absorbent resin composition (11) | 33 | 29 | 14.5 | 14.5 | 13.0 | 350 | 130 | 80 |
| Comparative Example 12 | Comparative water-absorbent resin composition (12) | 33 | 28 | 15.5 | 15.5 | 14.0 | 360 | 120 | 80 |

TABLE 2-continued

| | Water-absorbent resin composition | Absorption capacity without load (g/g) | Absorption capacity under the pressure of 1.9 KPa (g/g) | Amount of the hydrogen sulfide residue under wet (ppm) | | | Amount of wet ammonia residue (ppm) | | |
|---|---|---|---|---|---|---|---|---|---|
| | | | | 30 min | 60 min | 180 min | 10 min | 30 min | 60 min |
| Comparative Example 13 | Comparative water-absorbent resin composition (13) | 34 | 26 | 11.5 | 10.0 | 9.0 | 240 | 110 | 70 |

Particle size distribution of each water-absorbent resin composition and comparative resin composition was almost the same (the same within error range) as that of the water-absorbent resin used.

TABLE 3

| | Water-absorbent resin composition | Deodorizing test | | | |
|---|---|---|---|---|---|
| | | 0 hour later | 3 hours later | 6 hours later | 24 hours later |
| Example 1 | Water-absorbent resin composition (1) | 1.2 | 2.2 | 2.6 | 3.0 |
| Example 2 | Water-absorbent resin composition (2) | 1.3 | 2.2 | 2.5 | 3.0 |
| Example 3 | Water-absorbent resin composition (3) | 1.1 | 2.4 | 2.6 | 3.1 |
| Example 4 | Water-absorbent resin composition (4) | 1.3 | 2.3 | 2.5 | 3.1 |
| Example 5 | Water-absorbent resin composition (5) | 1.4 | 2.2 | 2.4 | 3.0 |
| Example 6 | Water-absorbent resin composition (6) | 1.3 | 2.4 | 2.7 | 3.0 |
| Example 7 | Water-absorbent resin composition (7) | 1.2 | 2.0 | 2.5 | 2.8 |
| Example 8 | Water-absorbent resin composition (8) | 1.3 | 2.2 | 2.5 | 2.9 |
| Example 9 | Water-absorbent resin composition (9) | 1.3 | 2.4 | 2.6 | 3.0 |
| Example 10 | Water-absorbent resin composition (10) | 1.8 | 2.6 | 2.9 | 3.2 |
| Example 11 | Water-absorbent resin composition (11) | 2.2 | 3.0 | 3.1 | 3.4 |
| Comparative Example 1 | Comparative water-absorbent resin composition (1) | 3.3 | 3.7 | 3.9 | 4.1 |
| Comparative Example 2 | Comparative water-absorbent resin composition (2) | 4.2 | 4.4 | 4.5 | 4.8 |
| Comparative Example 3 | Comparative water-absorbent resin composition (3) | 4.0 | 4.2 | 4.5 | 4.7 |
| Comparative Example 4 | Comparative water-absorbent resin composition (4) | 4.7 | 4.7 | 4.8 | 4.5 |
| Comparative Example 5 | Comparative water-absorbent resin composition (5) | 2.3 | 3.7 | 3.7 | 3.5 |
| Comparative Example 6 | Comparative water-absorbent resin composition (6) | 3.0 | 4.0 | 4.2 | 3.5 |
| Comparative Example 7 | Comparative water-absorbent resin composition (7) | 2.3 | 3.3 | 3.8 | 4.0 |
| Comparative Example 8 | Comparative water-absorbent resin composition (8) | 2.7 | 3.4 | 3.8 | 4.0 |
| Comparative Example 9 | Comparative water-absorbent resin composition (9) | 2.7 | 3.3 | 3.9 | 4.2 |
| Comparative Example 10 | Comparative water-absorbent resin composition (10) | 3.8 | 3.7 | 4.3 | 4.4 |
| Comparative Example 11 | Comparative water-absorbent resin composition (11) | 3.3 | 3.4 | 3.4 | 4.4 |
| Comparative Example 12 | Comparative water-absorbent resin composition (12) | 2.7 | 2.9 | 3.7 | 3.9 |
| Comparative Example 13 | Comparative water-absorbent resin composition (13) | 2.0 | 3.2 | 3.2 | 3.0 |

TABLE 4

| | Water-absorbent resin composition | Separation ratio (%) | Hygroscopic blocking ratio (mass %) |
|---|---|---|---|
| Example 1 | Water-absorbent resin composition (1) | 0 | 0 |
| Example 8 | Water-absorbent resin composition (8) | 0 | 0 |
| Example 9 | Water-absorbent resin composition (9) | 0 | 0 |
| Example 10 | Water-absorbent resin composition (10) | 0 | 0 |
| Comparative Example 4 | Comparative water-absorbent resin composition (4) | — | 100 |
| Comparative Example 5 | Comparative water-absorbent resin composition (5) | 0 | 100 |
| Comparative Example 6 | Comparative water-absorbent resin composition (6) | 21 | 100 |
| Comparative Example 7 | Comparative water-absorbent resin composition (7) | 100 | 39.7 |
| Comparative Example 8 | Comparative water-absorbent resin composition (8) | 38 | 0 |
| Comparative Example 9 | Comparative water-absorbent resin composition (9) | 0 | 0 |
| Comparative Example 10 | Comparative water-absorbent resin composition (10) | 100 | 0 |
| Comparative Example 11 | Comparative water-absorbent resin composition (11) | 100 | 98.8 |
| Comparative Example 12 | Comparative water-absorbent resin composition (12) | 100 | 51.3 |

TABLE 5

| | Water-absorbent product | Deodorizing test | | | |
|---|---|---|---|---|---|
| | | 0 hour later | 3 hours later | 6 hours later | 24 hours later |
| Example 11 | Water-absorbent product (1) | 1.2 | 2.0 | 2.4 | 2.8 |
| Example 12 | Water-absorbent product (2) | 1.2 | 1.9 | 2.2 | 2.5 |
| Example 13 | Water-absorbent product (3) | 1.2 | 1.9 | 2.2 | 2.5 |
| Example 14 | Water-absorbent product (4) | 1.2 | 2.2 | 2.6 | 3.0 |
| Comparative Example 14 | Comparative water-absorbent product (1) | 4.5 | 4.5 | 4.7 | 4.8 |
| Comparative Example 15 | Comparative water-absorbent product (2) | 2.5 | 3.6 | 3.7 | 4.0 |
| Comparative Example 16 | Comparative water-absorbent product (3) | 2.0 | 3.2 | 3.7 | 4.1 |
| Comparative Example 17 | Comparative water-absorbent product (4) | 2.3 | 35.0 | 3.6 | 3.6 |

The entire disclosure of Japanese Patent Application No. 2003-280373 filed on Jul. 25, 2003 including specification, claims, drawings, and summary are incorporated herein by reference in its entirety.

The invention claimed is:

1. A water-absorbent resin composition having the absorption capacity at 60 minutes toward 0.90 mass % sodium chloride aqueous solution under the pressure of 1.9 kPa not less than 20 g/g, comprising:
a plant component,
a water-absorbent resin obtained by polymerizing an unsaturated monomer having an acid group and/or a salt thereof, and
a complex oxide hydrate containing zinc and silicon, or zinc and aluminum, wherein the complex oxide hydrate constitutes 0.001 to 5 parts by weight per 100 parts by weight the absorbent resin, in which the mass ratio of the content of zinc and the content of silicon or aluminum is in the range of 50/50-99/1; the water-absorbent resin composition is in a granular state and contains particles exceeding 150 μm in diameter in a proportion of not less than 90 mass % of all the particles, exceeding 300 μm in diameter in a proportion of not less than 60 mass % of all the particles, and not exceeding 850 μm in diameter in 100 mass % of all the particles; the complex oxide hydrate is present on the surface of the water-absorbent resin; and the plant component is at least one compound selected from the group consisting of polyphenols, flavones and caffeines.

2. A water-absorbent resin composition having the absorption capacity at 60 minutes toward 0.90 mass % sodium chloride aqueous solution under the pressure of 1.9 kPa not less than 20 g/g, comprising:
a plant component,
a water-absorbent resin obtained by polymerizing an unsaturated monomer having an acid group and/or a salt thereof, and
a complex oxide hydrate containing zinc and silicon, or zinc and aluminum, wherein the complex oxide hydrate constitutes 0.001 to 5 parts by weight per 100 parts by weight the absorbent resin, in which the mass ratio of the content of zinc and the content of silicon or aluminum is in the range of 50/50-99/1; the water-absorbent resin composition is in a granular state and contains particles exceeding 150 μm in diameter in a proportion of not less than 90 mass % of all the particles, exceeding 300 μm in diameter in a proportion of not less than 60 mass % of all the particles, and not exceeding 850 μm in diameter in 100 mass % of all the particles; the complex oxide hydrate is present on the surface of the water-absorbent resin; and the plant component is at least one compound selected from the group consisting of tannins, tannic acid, gall, nutgall, and gallic acid.

3. A water-absorbent resin composition having the absorption capacity at 60 minutes toward 0.90 mass % sodium chloride aqueous solution under the pressure of 1.9 kPa not less than 20 g/g, comprising:
  a plant component,
  a water-absorbent resin obtained by polymerizing an unsaturated monomer having an acid group and/or a salt thereof, and
  a complex oxide hydrate containing zinc and silicon, or zinc and aluminum, wherein the complex oxide hydrate constitutes 0.001 to 5 parts by weight per 100 parts by weight the absorbent resin, in which the mass ratio of the content of zinc and the content of silicon or aluminum is in the range of 50/50-99/1; the water-absorbent resin composition is in a granular state and contains particles exceeding 150 μm in diameter in a proportion of not less than 90 mass % of all the particles, exceeding 300 μm in diameter in a proportion of not less than 60 mass % of all the particles, and not exceeding 850 μm in diameter in 100 mass % of all the particles; the complex oxide hydrate is present on the surface of the water-absorbent resin; and the plant component is contained in a range of 0.001-10 parts by weight based on 100 parts by weight of the water-absorbent resin.

4. A water-absorbent resin composition according to claim 1, wherein the absorbent resin is surface crosslinked with a surface crosslinking agent at a temperature in the range of 100 to 250° C.

5. A water-absorbent resin composition according to claim 2, wherein the absorbent resin is surface crosslinked with a surface crosslinking agent at a temperature in the range of 100 to 250° C.

6. A water-absorbent resin composition according to claim 3, wherein the absorbent resin is surface crosslinked with a surface crosslinking agent at a temperature in the range of 100 to 250° C.

7. An absorbent material for sanitary product comprising: a water-absorbent resin composition of claim 1 and hydrophilic fibers.

8. An absorbent material for sanitary product comprising: a water-absorbent resin composition of claim 2 and hydrophilic fibers.

9. An absorbent material for sanitary product comprising: a water-absorbent resin composition of claim 3 and hydrophilic fibers.

10. An absorbent product comprising: an absorbent material of claim 7, top-sheet possessing permeability to liquid, and back-sheet possessing impermeability to liquid.

11. An absorbent product comprising: an absorbent material of claim 8, top-sheet possessing permeability to liquid, and back-sheet possessing impermeability to liquid.

12. An absorbent product comprising: an absorbent material of claim 9, top-sheet possessing permeability to liquid, and back-sheet possessing impermeability to liquid.

13. A water-absorbent resin composition according to claim 1, wherein the plant component is at least one of polyphenols and flavones.

14. A water-absorbent resin composition according to claim 2, wherein the plant component is at least one of gall, nutgall, and gallic acid.

15. A water-absorbent resin composition according to claim 1, wherein the complex oxide hydrate has a separation ratio of 0 to 20%.

16. A water-absorbent resin composition according to claim 2, wherein the complex oxide hydrate has a separation ratio of 0 to 20%.

17. A water-absorbent resin composition according to claim 3, wherein the complex oxide hydrate has a separation ratio of 0 to 20%.

18. A water-absorbent resin composition according to claim 1, wherein the absorbent resin composition has a hygroscopic blocking ratio of 0 to 30 mass %.

19. A water-absorbent resin composition according to claim 2, wherein the absorbent resin composition has a hygroscopic blocking ratio of 0 to 30 mass %.

20. A water-absorbent resin composition according to claim 3, wherein the absorbent resin composition has a hygroscopic blocking ratio of 0 to 30 mass %.

* * * * *